(12) United States Patent
Löser et al.

(10) Patent No.: US 10,695,526 B2
(45) Date of Patent: Jun. 30, 2020

(54) VENTILATION SYSTEM

(71) Applicant: Dräger Medical GmbH, Lübeck (DE)

(72) Inventors: Judith Löser, Lübeck (DE); Götz Kullik, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 1329 days.

(21) Appl. No.: 14/652,920

(22) PCT Filed: Dec. 18, 2013

(86) PCT No.: PCT/EP2013/077035
§ 371 (c)(1),
(2) Date: Jun. 17, 2015

(87) PCT Pub. No.: WO2014/095962
PCT Pub. Date: Jun. 26, 2014

(65) Prior Publication Data
US 2015/0328417 A1    Nov. 19, 2015

(30) Foreign Application Priority Data

Dec. 18, 2012  (DE) .................. 10 2012 024 672

(51) Int. Cl.
*A61M 16/20*  (2006.01)
*A61N 1/39*  (2006.01)
(Continued)

(52) U.S. Cl.
CPC ......... *A61M 16/205* (2014.02); *A61H 31/006* (2013.01); *A61M 16/024* (2017.08);
(Continued)

(58) Field of Classification Search
CPC .............. A61M 16/205; A61M 16/204; A61M 16/024; A61M 16/0816;
(Continued)

(56) References Cited

U.S. PATENT DOCUMENTS 4,326,507 A    4/1982  Barkalow
4,401,115 A *  8/1983  Monnier ........... A61M 16/1015
                                                  128/204.23
(Continued)

FOREIGN PATENT DOCUMENTS

CN    1518470 A    8/2004
CN    101023902 A   8/2007
(Continued)

*Primary Examiner* — Timothy A Stanis
*Assistant Examiner* — Jonathan S Paciorek
(74) *Attorney, Agent, or Firm* — McGlew and Tuttle, P.C.

(57) ABSTRACT

A respiration device (1) supports cardio-pulmonary resuscitation (CPR) and a method for operating a respiration device (1) supports cardio-pulmonary resuscitation (CPR). The respiration device (1) has a control and regulation unit (7) in order to actuate an expiratory metering unit (3), and an inspiratory metering unit (2) such that, in a first phase, a current value of pressure is increased relative to a first pre-defined value (16) and such that, in a second phase, the current value of the pressure is reduced relative to the first pre-defined value (16).

14 Claims, 12 Drawing Sheets

(51) Int. Cl.
*A61H 31/00* (2006.01)
*A61M 16/00* (2006.01)
*A61M 16/10* (2006.01)
*A61M 16/08* (2006.01)
*A61M 16/12* (2006.01)

(52) U.S. Cl.
CPC ......... *A61M 16/204* (2014.02); *A61N 1/3987* (2013.01); *A61H 31/005* (2013.01); *A61H 31/007* (2013.01); *A61H 2201/5071* (2013.01); *A61H 2230/045* (2013.01); *A61H 2230/065* (2013.01); *A61H 2230/206* (2013.01); *A61H 2230/208* (2013.01); *A61H 2230/305* (2013.01); *A61H 2230/405* (2013.01); *A61M 16/0051* (2013.01); *A61M 16/0066* (2013.01); *A61M 16/085* (2014.02); *A61M 16/0833* (2014.02); *A61M 16/125* (2014.02); *A61M 16/127* (2014.02); *A61M 2016/0021* (2013.01); *A61M 2016/0027* (2013.01); *A61M 2016/0036* (2013.01); *A61M 2016/0039* (2013.01); *A61M 2016/0042* (2013.01); *A61M 2016/103* (2013.01); *A61M 2016/1025* (2013.01); *A61M 2202/0208* (2013.01); *A61M 2205/054* (2013.01); *A61M 2205/18* (2013.01); *A61M 2205/35* (2013.01); *A61M 2205/502* (2013.01); *A61M 2205/581* (2013.01); *A61M 2205/583* (2013.01); *A61M 2205/8206* (2013.01); *A61M 2230/04* (2013.01); *A61M 2230/10* (2013.01); *A61M 2230/202* (2013.01); *A61M 2230/205* (2013.01); *A61M 2230/30* (2013.01); *A61M 2230/432* (2013.01); *A61M 2230/435* (2013.01); *A61M 2230/60* (2013.01); *A61N 1/39* (2013.01)

(58) Field of Classification Search
CPC ...... A61M 2016/0021; A61M 16/0833; A61M 16/085; A61M 16/125; A61M 16/127; A61M 16/0051; A61M 16/0066; A61H 31/006; A61H 2230/065; A61H 2230/206; A61H 2230/208; A61H 2230/305; A61H 2230/405; A61H 31/005; A61H 31/007; A61H 2201/5071; A61H 2230/045; A61N 1/3987

See application file for complete search history.

(56) References Cited

U.S. PATENT DOCUMENTS

| | | | | |
|---|---|---|---|---|
| 6,062,219 | A | * | 5/2000 | Lurie ................ A61M 16/0084 128/205.13 |
| 6,155,257 | A | | 12/2000 | Lurie et al. |
| 6,171,267 | B1 | * | 1/2001 | Baldwin, II ........... A61H 31/00 601/106 |
| 8,151,790 | B2 | | 4/2012 | Lurie et al. |
| 2001/0011159 | A1 | | 8/2001 | Cantrell et al. |
| 2004/0058305 | A1 | | 3/2004 | Lurie et al. |
| 2006/0111749 | A1 | * | 5/2006 | Westenskow ......... A61M 16/00 607/5 |
| 2008/0228096 | A1 | * | 9/2008 | Jaffe .................... A61B 5/0836 600/532 |
| 2008/0257344 | A1 | * | 10/2008 | Lurie ................ A61M 16/0048 128/203.11 |
| 2010/0224189 | A1 | * | 9/2010 | Lorenzen .......... A61M 16/0096 128/204.21 |
| 2010/0319691 | A1 | | 12/2010 | Lurie et al. |
| 2010/0326443 | A1 | | 12/2010 | Steen et al. |
| 2011/0201957 | A1 | * | 8/2011 | Zhou .................... A61B 5/0836 600/532 |

FOREIGN PATENT DOCUMENTS

| | | |
|---|---|---|
| CN | 101970984 A | 2/2011 |
| CN | 102802709 A | 11/2012 |
| DE | 8 418 594 U1 | 11/1984 |
| DE | 4 007 361 A1 | 9/1991 |
| DE | 203 15 975 U1 | 4/2004 |
| DE | 10 2009 012146 A1 | 9/2010 |
| DE | 102011007964 A1 | 7/2011 |
| EP | 0 029 352 A1 | 5/1981 |
| EP | 0 509 773 A1 | 10/1992 |
| EP | 0 509 773 B1 | 1/1998 |
| EP | 2 198 823 A1 | 6/2010 |
| EP | 2 343 097 A2 | 7/2011 |
| WO | 2010/059049 A2 | 5/2010 |
| WO | 2012/131586 A1 | 10/2012 |

* cited by examiner

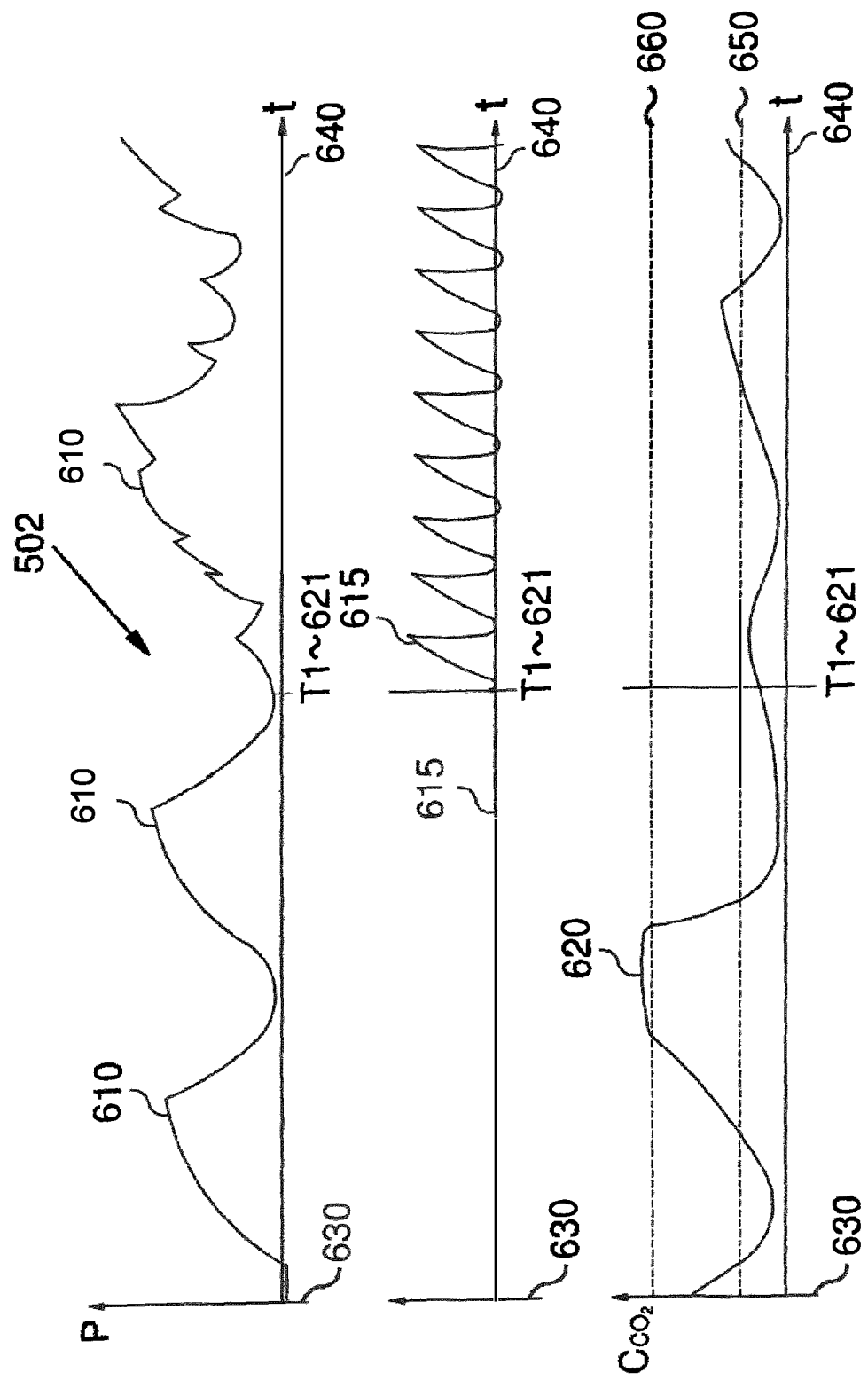

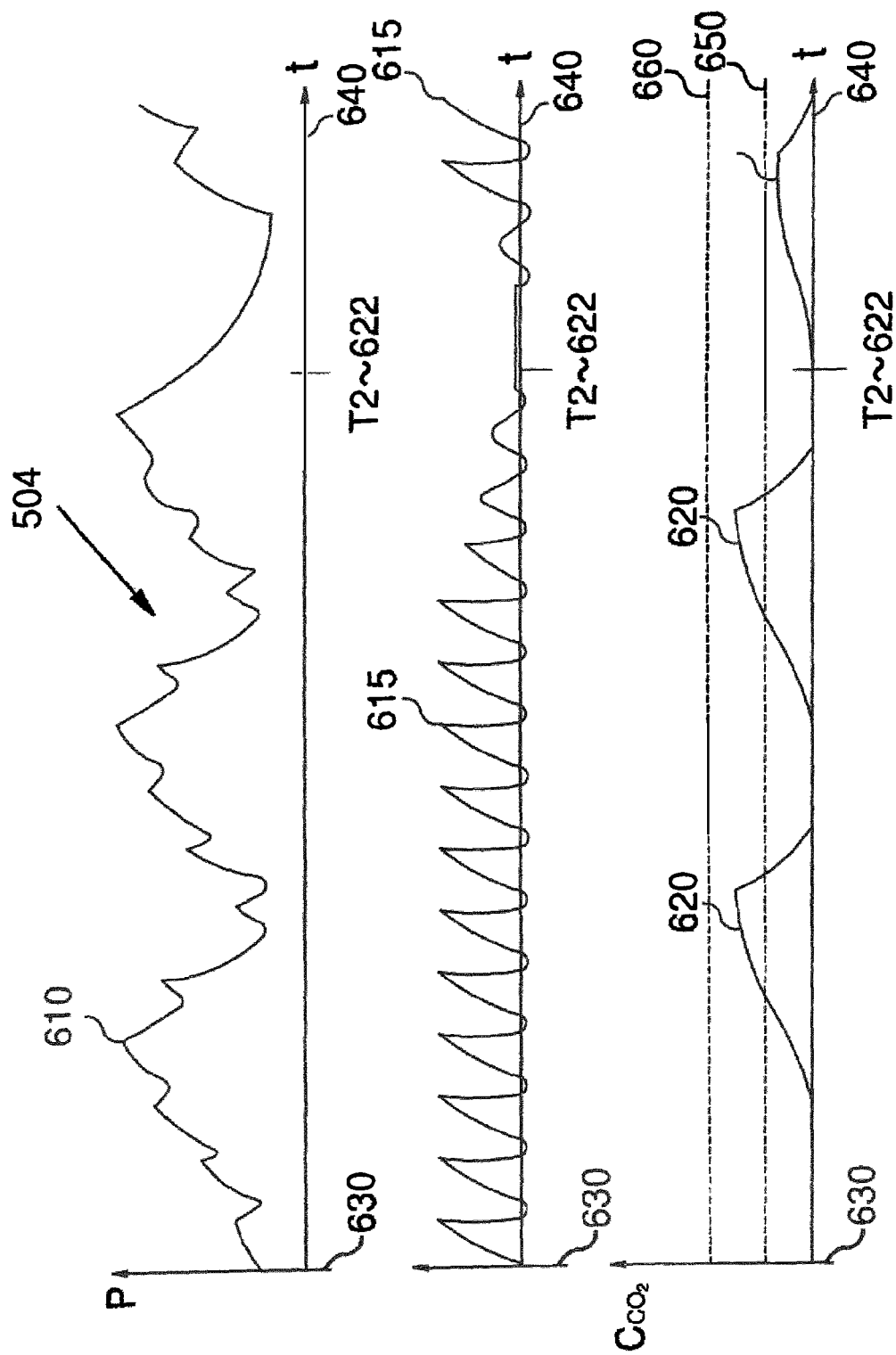

VENTILATION SYSTEM

CROSS REFERENCE TO RELATED APPLICATIONS

This application is a United States National Phase Application of International Application PCT/EP2013/077035 filed Dec. 18, 2013 and claims the benefit of priority under 35 U.S.C. § 119 of German Patent Application 10 2012 024 672.2 filed Dec. 18, 2012, the entire contents of which are incorporated herein by reference.

FIELD OF THE INVENTION

The present invention pertains to a ventilation system (also known as a respiration system) with a gas supply device with a tube arrangement, wherein the tube arrangement has a patient port for connection to a patient in order to send gas from the gas supply device to the patient and to remove gas exhaled by the patient, with a gas flow-controlling device from the gas supply device to the patient port and for controlling the gas flow away from the patient port, with a sensor unit, which is arranged in the tube arrangement and is set up to detect parameters of the gas supplied to the patient and exhaled by the patient, and with a control and regulation unit for controlling the gas supply device and the gas flow-controlling device, which is connected with the gas supply device, the gas flow-controlling device and the sensor unit.

BACKGROUND OF THE INVENTION

A situation in which it is necessary both to ventilate a patient and to perform a cardiopulmonary resuscitation on that patient frequently occurs in case of the mechanical ventilation of patients, especially in emergency use. The patient is mechanically ventilated, as a rule, via a mask or an endotracheal tube by means of an emergency ventilator.

On the one hand, emergency ventilators, which make the mechanical ventilation of the patient possible in emergency situations, are known from the state of the art. Emergency ventilators are characterized in that they can be used as mobile, portable, autarchic devices independently from external electric power and breathing gas supply. Emergency ventilators are shown in DE 4007361 A1 as well as DE 20315975 U1. In addition, portable and mobile ventilators are known from the field of assisting therapy for both clinical and home use. Thus, DE 8418594 U1 describes a device for acute intervention in asthma, cardiovascular accidents, myocardial infarctions, circulatory symptoms and even for long-term use in the therapy of chronic bronchitis. On the other hand, devices are known that assist the user in performing cardiopulmonary resuscitation (CPR). Cardiopulmonary resuscitation (CPR) is performed by a helping and rescuing person, optionally with assistance of a second person, manually as an alternation between pressure massage of the chest and rescue breathing by means of mouth-to-mouth or mouth-to-nose resuscitation. The alternation between pressure massage and rescue breathing is usually performed at a continuous rhythm of 30 pressure massages of the chest alternating with 2 rescue breaths or at a continuous rhythm of 15 chest massages alternating with 2 rescue breaths until the patient's cardiovascular system resumes functioning on its own, i.e., there is a regular heartbeat again. The rescue breathing is subsequently continued until the patient becomes able to breathe on his own again. We also speak of a 30-to-2 cardiopulmonary resuscitation (CPR), but it has additional variations as well. One person performs alternatingly the chest massages and the rescue breathing in case of the so-called one-rescuer method, and one person performs the chest massage and the second person the rescue breathing in case of the so-called two-rescuer method. Devices, which assist the 30-to-2 rhythm by optical and/or acoustic signal generation and enable the person/persons to concentrate essentially on the performance of the cardiopulmonary resuscitation (CPR) and the patient's status, are available as an aid for the first and/or second person.

Devices for assisting the helping and rescuing persons are described in US 2006 111 749 A1.

Furthermore, training devices and simulators for clinical staff for training in the performance of pressure massage of the chest with correct pressure alternating rhythmically properly with the rescue breathing with correct ventilation (quantity of air) are known. Such training devices and simulators are described in US 2004 058 305 A1.

U.S. Pat. No. 8,151,790 described as another state of the art a valve that may be arranged between a ventilator and a patient for simultaneous use with cardiac massage in order to change the filling of the lungs over time and the pressure in the lungs, as well as the changes in pressure over time in relation to the time frame of inspiration and expiration phases, which time grid is supplied by the ventilator.

A cardiopulmonary device for resuscitating (CPR) a patient for performing cardiac massage and with a device for controlling a ventilator is known from EP0029352 B1. The ventilator is actuated here such that outflow of air from the patient's lungs is prevented from time to time synchronously with the cardiac massage during the transportation of blood from the heart into the patient's body (systole).

U.S. Pat. No. 6,155,257 shows a ventilator as well as a method for operating the ventilator in conjunction with a cardiopulmonary resuscitation (CPR), wherein the ventilation is adapted to the cardiopulmonary resuscitation (CPR). A valve is provided, which is arranged in the gas flow to the patient, in order to delay or prevent the inflow of gas into the patient's lungs until the pressure in the patient's chest cavity has fallen below a predetermined vacuum value relative to the ambient pressure.

When an emergency ventilator is used, the cardiopulmonary resuscitation (CPR) is performed in a usual emergency situation by a helper simultaneously with and superimposed to, but essentially independently from the ventilation. Cardiac massage (CM) is necessary for maintaining the patient's circulatory function in order to supply essentially the brain and other body parts with oxygen by maintaining the blood flow from the heart over the lungs into the body parts to avoid damage, especially permanent damage developing in the brain relatively immediately in case of oxygen deficiency and thus to ensure the supply of oxygen from the lungs into the cells of the body parts and a removal of carbon dioxide from the cells of the body. It is therefore additionally necessary to supply fresh breathing air with a sufficient percentage of oxygen to the lungs. This supply may be achieved by manual rescue breathing by a helper with an oxygen concentration of about 16% or by the use of an emergency ventilator with variable and adjustable oxygen supply.

It is advantageous for the use of cardiac massage that the heart cannot yield when pressing in the chest. Since the possibilities for yielding are limited relatively constantly essentially by the anatomy of the ribs and the organs directly below the chest cavity (stomach, spleen, liver), the expansion space that remains available for yielding is the three-dimensional area of the lungs. Whenever the lungs are emptied completely to the extent that only the so-called functional residual capacity (FRC) is filled with air, i.e., at the end of each expiration phase, the so-called expiration phase, the three-dimensional area in which the heart can yield has its maximum. If the heart in the chest cavity has a possibility of expanding, the effect of the cardiac massage is weaker, despite the application of massive force on the patient's chest by the helper, relative to the delivery of blood from the heart to the body parts, especially the brain, which is brought about by the cardiac massage, than when this space is not available for yielding. As a consequence of this, there is a less effective exchange between the oxygen present in the blood and carbon dioxide and, associated herewith, there is especially a less adequate oxygen supply for the brain, which leads to an increase in the probability of permanent damage for the patient. It is therefore advantageous when performing cardiac massage that the lungs be filled extensively or not emptied substantially during the phase of compression of the cardiac massage, so that the three-dimension area in which the heart can yield is minimized and thus the effect of the cardiac massage and hence indirectly also the pressure of the blood flowing into the body (systolic blood pressure) are increased and the exchange between the oxygen present in the blood and carbon dioxide is improved.

Furthermore, it is advantageous when performing the cardiac massage that the patient's lungs are emptied nearly completely, except for the volume of the functional residual capacity, during the phase of decompression of the cardiac massage, and even a slight vacuum is ideally brought about in the lungs in relation to the ambient pressure in order to assist the backflow of the blood to the heart. Thus assistance arises from the fact that sufficient space is available for the heart and the venous blood vessels leading to the heart in the chest cavity of the patient for the backflow of blood, and the nearly emptied lungs will not fill out this space. An additional aspect is that the blood pressure of the blood flowing back (diastolic blood pressure) is not affected by the ventilation pressure prevailing in the lungs and is possibly increased thereby. As a consequence of the assistance of the backflow of the blood to the heart, an improvement in the blood perfusion and the exchange of blood in the heart as a whole will thus lead indirectly to an improvement of the exchange of oxygen and carbon dioxide in the blood circulation. As a consequence of the improved exchange of oxygen and carbon dioxide in the blood, the risk of permanent damage to the patient, especially to the patient's brain, will decrease. If a conventional cardiopulmonary resuscitation (CPR) is performed according to the one-rescuer method, the 30-to-2 rhythm is used with the use of ventilation through a face mask. Cardiac massage and ventilation are not performed simultaneously here. As soon as an additional rescuer, especially an emergency physician, becomes available in an emergency situation, the mask is replaced with an endotracheal tube, and the endotracheal tube is connected to an emergency ventilator by means of a tube connection. Such an endotracheal tube will be called "tube" for short in the course of the further description of the present application. This has the advantage that the access to the lungs remains free, because it is ensured by the tube that no material aspirated by the patient from the gastrointestinal region can be transported into the patient's lungs during the performance of the rescue breathing. As soon as the access to the patient's airways is ensured, continuous ventilation is performed by means of the ventilator. At the same time, the cardiac massage is continued continuously by a rescuer or a suitable device.

A suitable device for applying the mechanical cardiac massage to the chest of a patient is described, for example, in EP0509773 B1.

The continuous compressions of the chest cavity as the effect of the cardiac massage affect, contrary to the cardiopulmonary resuscitation (CPR) with an alternation between cardiac massage and ventilation, for example according to the 30 (cardiac massages) to 2 (ventilation cycles) rhythm, the 15-to-2 rhythm or the 10-to-2 rhythm, both the manner of filling of the lungs by the ventilator and the resulting pressure changes in the lungs.

Thus, there is a superimposition of the pressure changes of expiration and inspiration, caused by the ventilation and the selected form of ventilation (ventilation mode), and the compressions caused by the cardiac massage in the curve describing the changes in the measured ventilation pressure during the operation of the ventilator. Three general basic ventilation forms, variants of pressure-regulated ventilation forms, variants of volume-regulated ventilation forms, variants of flow-regulated ventilation forms, as well as combinations thereof, for example, a pressure-regulated ventilation form with volume guarantee and maximum flow limitation, are provided by a ventilator according to the state of the art for ventilating a patient. This superimposition due to and of the compressions of the cardiac massage represents an additional marginal condition and an interference variable for the regulation of the ventilation pressure, especially in the pressure-regulated forms of ventilation.

SUMMARY OF THE INVENTION

An object of the present invention is to provide a ventilation system for assisting cardiopulmonary resuscitation (CPR) as well as a suitable method for assisting cardiopulmonary resuscitation (CPR).

This object is accomplished by a ventilation system with a gas supply device, with a tube arrangement, wherein the tube arrangement has a patient port for connection to a patient in order to send gas from the gas supply device to the patient and to remove gas exhaled by the patient, with gas flow-controlling device from the gas supply device to the patient port and for controlling the gas flow away from the patient port, with a sensor unit, which is arranged in the tube arrangement and is set up to detect parameters of the gas supplied to the patient and exhaled by the patient, with a control and regulation unit for controlling the gas supply device and the gas flow-controlling device, which is connected to the gas supply device, to the gas flow-controlling device and to the sensor unit, wherein the control and regulation unit is designed such that in a first mode of operation, the gas flow-controlling device is actuated during an expiration phase such that the pressure of the gas exhaled by the patient at the patient port is described by a first curve, and the gas flow-controlling device is actuated during an inspiration phase such that the pressure of the gas supplied to the patient at the patient port is described by a second curve, wherein the expiration phase and the inspiration phase follow one another continuously alternatingly, wherein the control and regulation unit is designed to have a second mode of operation, wherein the control and regulation unit is designed such that in the second mode of operation, the gas flow-controlling device is actuated during the expiration phase such that the pressure of the gas exhaled by the patient at the patient port is described by a third curve that is increased compared to the first curve at least during one section of the expiration phase, and the gas flow-controlling device is actuated during an inspiration phase such that the pressure of the gas supplied to the patient at the patient port is described by a fourth curve, which is reduced compared to the second curve, at least during one section of the inspiration phase, and a device is provided for switching over the control and regulation unit between the first mode of operation and the second mode of operation.

The ventilation system according to the present invention thus can operate in a first mode of operation, in which the changes in the pressure of the breathing gas with which the patient is supplied are described by a first and second curve during the inspiration phase and the expiration phase, respectively. This means that the pressure described by the first curve and the second curve consecutively assume over time a series of values, which are stored in the control and regulation unit. These curves are provided for a normal ventilation of a patient and may vary depending on the patient.

In addition, the ventilation system according to the present invention and the ventilation system control and regulation unit are designed (configured), however, such that a second mode of operation is provided, in which curves differing from the first curve and the second curve are selected during both the inspiration phase and the expiration phase, at least in some sections, for the pressure that the breathing gas being supplied to the patient has during these phases.

These second and third curves are selected such that the curve of the pressure, i.e., the third curve, is increased during the expiration phase compared to the curve in the first mode of operation. This means that the values obtained for the pressure of the breathing gas will then be higher during the expiration phase of the second mode of operation than those that are obtained at corresponding times in the first mode of operation.

If the second mode of operation is selected when a cardiopulmonary resuscitation is being performed on the patient, the pressure in the lungs is increased during the expiration phase relative to the normal ventilation in the first mode of operation. The consequence of this is that the heart can yield less markedly into the area of the lungs during the compression of the chest associated with the cardiopulmonary resuscitation and is thus compressed more strongly, so that more blood is pressed out of the area of the heart.

Moreover, the pressure curve during the inspiration phase, i.e., the fourth curve by definition, is selected to be such in the second mode of operation that it assumes lower values at least in some sections compared to the curve in the first mode of operation, i.e., the second curve. This also means here that the values obtained for the pressure of the breathing gas at the patient port are lower, at least in some sections, than those obtained at corresponding times during the inspiration phase in the first mode of operation. This fourth curve is consequently lowered relative to the second curve. If the second mode of operation is activated together with a cardiopulmonary resuscitation, this will lead to an initially greater contraction of the patient's lungs and to the heart being able to expand to a greater extent, so that more blood will flow back into the blood vessels of the heart than this would be the case if the patient were ventilated according to the first mode of operation.

It is consequently achieved due to the provision of two modes of operation in the ventilation system according to the present invention that the operation of this ventilation system can be adapted to whether the patient is undergoing a cardiopulmonary resuscitation or not, and the effect of the resuscitation measure is optimized hereby.

The control and regulation unit is preferably designed to actuate the gas flow-controlling device such that the expiration phase and the inspiration phase have two consecutive partial phases in the second mode of operation, and the pressure of the gas being exhaled by the patient at the patient port is described by the third curve during the first partial phase of the expiration phase, the pressure of the gas being exhaled by the patient at the patient port is described by a curve corresponding to the first curve during the second partial phase of the expiration phase, the pressure of the gas being supplied to the patient at the patient port is described by the fourth curve during the first partial phase of the inspiration phase, and the pressure of the gas being supplied to the patient at the patient port is described by a curve corresponding to the second curve during the second partial phase of the inspiration phase.

The ventilation of the patient is changed during the application of a cardiopulmonary resuscitation in this preferred embodiment of the ventilation system such that the pressure of the breathing gas at the patient port during the inspiration phase is increased in the second mode of operation that is now triggered only at the start, namely, in the first partial phase, while it is described in the further part of the inspiration phase, namely, the second partial phase, by the same curve as during normal operation, i.e., in the first mode of operation. The expiration phase is likewise divided analogously into two partial phases in this preferred embodiment, but a reduction of the pressure relative to the first mode of operation takes place here only in the chronologically first partial phase, while the pressure curve in the second partial phase corresponds to that also seen during the normal ventilation, i.e., in the first mode of operation.

Due to the fact that changes occur in the pressure curve only at the start of the inspiration phase and expiration phase, the desired effect of increased blood circulation at the heart is achieved, on the one hand, but the patient's breathing is not made difficult over the entire expiration phase and inspiration phase.

To achieve the pressure increase at the start of the expiration phase as well as the reduction at the start of the inspiration phase, it is preferably possible for the control and regulation unit to be designed to actuate the gas flow-controlling device such during the expiration phase, for the third pressure curve to be obtained by increasing a desired pressure value. In addition, the control and regulation unit may be designed to actuate the gas flow-controlling device during the inspiration phase such that the fourth pressure curve is obtained by reducing a desired pressure value.

As an alternative to this, the tube arrangement may have a breathing gas outlet line, which leads away from the patient port and can be opened and closed relative to the patient port by an expiration valve, the expiration valve being connected to the control and regulation unit and the control and regulation unit being designed to actuate the expiration valve during the expiration phase such that it is opened with a time delay relative to the start of the expiration phase. In the same manner, the tube arrangement may have a breathing gas supply line, which leads from the gas supply device to the patient port and can be opened and closed relative to the patient port by an inspiration valve, the inspiration valve being connected to the control and regulation unit, the control and regulation unit being designed to actuate the inspiration valve during the inspiration phase such that it is opened with a time delay relative to the start of the inspiration phase.

The pressure increase at the start of the expiration phase and the reduction at the start of the inspiration phase are achieved in a relatively simple manner in this alternative by the corresponding valves in the tube arrangement being opened with a delay, so that the patient's breathing and the absence of outflow or inflow of gas leads to the pressure change relative to the first and second curves.

A switch over device, with which the user can switch the control and regulation unit over between the first mode of operation and the second mode of operation, is preferably provided at the ventilation system. The switch over device may also be embodied in the form of software, via which the system is controlled and which will then provide a function by which a user can switch over between the modes of operation on a user interface.

As an alternative or in addition, the control and regulation unit may be designed to determine from the parameters detected by the sensor unit whether a cardiopulmonary resuscitation is being performed on a patient connected to the patient port, and to select the second mode of operation when parameters corresponding to a cardiopulmonary resuscitation are present. This will make it possible to switch automatically over to the mode of operation that optimizes the effectiveness of the cardiopulmonary resuscitation.

In a likewise preferred manner, the automatic detection of a cardiopulmonary resuscitation may take place by the control and regulation unit being designed to monitor the time curve of the pressure at the patient port during the inspiration phase and the expiration phase and to determine from the time curve of the pressure whether a cardiopulmonary resuscitation is being performed on the patient. The pressure signal, in particular, may be monitored here for regularly occurring peaks, and this can be used as a criterion for determining that a cardiopulmonary resuscitation is being performed.

In another preferred embodiment, the sensor unit has a sensor, which is designed to determine the $CO_2$ content in the air being exhaled by the patient during the expiration phase, the control and regulation unit being designed to determine from the $CO_2$ content of the air being exhaled by the patient whether a cardiopulmonary resuscitation is being performed on the patient.

In addition, it is also possible to determine whether a cardiopulmonary resuscitation is being performed on the patient on the basis of the signal of a sensor present at the ventilation system for measuring the oxygen saturation in the blood ($SPO_2$), which can be connected to the patient.

Finally, the sensor unit may have a sensor that is designed to determine the oxygen content in the air being exhaled by the patient during the expiration phase, the control and regulation unit being designed to determine from the oxygen content in the air being exhaled by the patient whether a cardiopulmonary resuscitation is being performed on the patient.

In another preferred embodiment, the ventilation system has a display unit, which is connected to the control and regulation unit, the control and regulation unit being designed to generate a first alarm message on the display unit in the first mode operation when a parameter detected by the sensor unit exceeds or falls below a threshold value, and the control and regulation unit being designed not to generate an alarm message or to send a second alarm message different from the first alarm message when the parameter detected by the sensor unit falls below or exceeds the threshold value in the second mode of operation.

The fact that the cardiopulmonary resuscitation affects the parameters detected by the sensor unit, for example, the pressure or the $CO_2$ content, is taken into account by this design. Alarm settings that are meaningful in the first mode of operation, in which the patient is being ventilated normally, no longer make any sense in the second mode of operation during a cardiopulmonary resuscitation, so that an alarm generated by the display unit is no longer meaningful, but it rather disturbs the user. This is taken into account in this embodiment.

If the display unit has acoustic signal device for sending an acoustic alarm, the first alarm message comprising a first acoustic alarm, the second alarm message cannot comprise an acoustic alarm, or it may comprise a second acoustic alarm, which is different from the first one and whose volume is reduced relative to the first acoustic alarm.

In another preferred embodiment or combined with the embodiment explained above, a display unit is provided, and the control and regulation unit is designed to monitor a parameter detected by the sensor unit in the second mode of operation and to generate a first message by the display unit when the parameter falls below a first threshold value and to generate a second message by the display unit when the parameter exceeds the first threshold value and falls below a second threshold value that is higher than the first threshold value, and to generate a third message by the display unit when the parameter exceeds the second threshold value, the first, second and third messages being different from one another. In particular, the sensor unit may have a sensor that is designed to determine the $CO_2$ content in the air being exhaled by the patient during the expiration phase, the $CO_2$ content in the air being exhaled by the patient being the parameter being monitored.

In such an embodiment, the user is informed by the different messages of whether the parameter in question is in a possibly desired range between the first and second threshold values or outside that range. In case of the $CO_2$ in the exhaled air, the first threshold value may be selected such that a measured value below that threshold indicates that the cardiopulmonary resuscitation shows no sufficient effect and it may possibly not being carried out correctly. The second threshold value may be selected such that if the measured $CO_2$ content is above it, the cardiopulmonary resuscitation can be ended because the patient can breathe on his own. The second message now shows that the cardiopulmonary resuscitation is being performed correctly but must be continued, while the third message shows to the user that the cardiopulmonary resuscitation can be ended.

As an alternative to a parameter of the breathing air, a sensor for measuring the oxygen saturation in the blood ($SPO_2$), which may be connected to the patient, may be provided at the ventilation system for the above-mentioned purpose, the control and regulation unit being designed to monitor the oxygen saturation in the blood ($SPO_2$) in the second mode of operation and to trigger a first message by the display unit when the oxygen saturation in the blood ($SPO_2$) falls below a first threshold value, to trigger a second message by the display unit when the oxygen saturation in the blood ($SPO_2$) exceeds the first threshold value and falls below a second threshold value that is higher than the first threshold value, and to trigger a third message by the display unit when the oxygen saturation in the blood ($SPO_2$) exceeds the second threshold value, the first, second and third messages being different from one another.

Finally, the ventilation system may have a device for automatically performing a cardiopulmonary resuscitation, which device is connected to the control and regulation unit, the control and regulation unit being designed (configured)

to switch over from the first to the second mode of operation in case of activation of the device for performing a cardiopulmonary resuscitation.

In addition, it is possible that the ventilation system has a voltage generator for generating voltage pulses, which is connected to the control unit, the voltage generator being provided with electrodes for connection to a patient.

According to the present invention, the ventilation method described below can, in addition, be carried out, a ventilation system used for this having the following components:

A gas supply device; a tube arrangement, the tube arrangement having a patient port for connection to a patient in order to send gas from the gas supply unit to the patient and to remove gas being exhaled by the patient; gas flow-controlling device from the gas supply device to the patient port and for guiding the gas flow away from the patient port; and a sensor unit, which is arranged in the tube arrangement and is set up to detect parameters of the gas supplied to the patient and exhaled by the patient.

In a first mode of operation, the gas flow-controlling device are actuated according to the present invention during an expiration phase such that the pressure of the gas being exhaled by the patient at the patient port is described by a first curve, and gas flow-controlling device are actuated during an inspiration phase such that the pressure of the gas being supplied to the patient at the patient port is described by a second curve, the expiration phase and the inspiration phase following one another alternatingly continuously.

Further, there is a second mode of operation according to the present invention, in which the gas flow-controlling device are actuated during the expiration phase such that the pressure of the gas being exhaled by the patient at the patient port is described, at least during a section of the expiration phase, by a third curve, which is increased compared to the first curve, and the gas flow-controlling device are actuated during an inspiration phase such that the pressure of the gas being supplied to the patient at the patient port is described, at least during a section of the inspiration phase, by a fourth curve which is reduced compared to the second curve.

Finally, there is a switch over from the first to the second mode of operation when a cardiopulmonary resuscitation is performed.

As was already explained in connection with the ventilation system according to the present invention, whether a cardiopulmonary resuscitation is being performed on the patient is taken into account in the method according to the present invention as well. If cardiopulmonary resuscitation is being performed, the second mode of operation can be activated, in which the pressure is increased at least in some sections during the expiration phase in order to make it difficult for the heart to yield into the area of the lungs. In addition, the pressure is reduced during the inspiration phase at least in some sections relative to the first mode of operation, which takes place during a normal ventilation, in order to achieve that a large amount of blood will flow into the cardiac vessels.

In a preferred embodiment of the ventilation method according to the present invention, the expiration phase and the inspiration phase have two consecutive partial phases in the second mode of operation, the pressure of the gas being exhaled by the patient at the patient port being described in the first partial phase of the expiration phase by the third curve, the pressure of the gas being exhaled by the patient at the patient port being described in the second partial phase of the expiration phase by a curve corresponding to the first curve, the pressure of the gas being supplied to the patient at the patient port being described in the first partial phase of the inspiration phase by the fourth curve, and the pressure of the gas being supplied to the patient at the patient port being described during the second partial phase of the inspiration phase by a curve corresponding to the second curve. The pressure curve is modified only at the start of the expiration phase and the inspiration phase in the second mode of operation in this embodiment, while the curve otherwise remains unchanged compared to the first mode of operation.

Further, the gas flow-controlling device may be actuated in one embodiment of the method such that the third and/or fourth pressure curve are obtained by increasing or decreasing a desired pressure value.

In an alternative hereto, the method according to the present invention may be carried out with a ventilation system whose tube arrangement has a breathing gas outlet line, which leads away from the patient port and can be opened and closed in relation to the patient port by an expiration valve, as well as a breathing gas supply line, which leads from the gas supply device to the patient port and can be opened and closed in relation to the patient port by an inspiration valve. The expiration valve can then be actuated in the second mode of operation such that it is opened with a time delay relative to the start of the expiration phase and that the inspiration valve is actuated such that it is opened with a time delay relative to the start of the inspiration phase.

The pressure increase and the pressure reduction at the start of the expiration phase and inspiration phase is achieved in this embodiment by these being achieved by the breathing of the patient.

Furthermore, the method according to the present invention may be designed such that it is determined from the parameters detected by the sensor unit whether a cardiopulmonary resuscitation is being carried out on a patient connected to the patient port, and the second mode of operation is selected when parameters corresponding to a cardiopulmonary resuscitation are present. In particular, the time curve of the pressure at the patient port can be monitored during the inspiration phase and the expiration phase, and it is determined from the time curve of the pressure whether a cardiopulmonary resuscitation is being carried out on the patient.

As an alternative or in addition, a sensor, which is designed to determine the $CO_2$ content in the air being exhaled by the patient during the expiration phase, may be provided in the ventilation system, and it is determined from the $CO_2$ content in the air being exhaled by the patient whether a cardiopulmonary resuscitation is being performed on the patient. It is, however, also conceivable that, in addition or as an alternative, the ventilation system has a sensor for measuring the oxygen saturation in the blood ($SPO_2$), which may be connected to a patient, and it is determined from the value of the oxygen saturation in the blood whether a cardiopulmonary resuscitation is being carried out on the patient. Finally, it is also possible that the sensor unit has a sensor that is designed to determine the oxygen content in the air being exhaled by the patient during the expiration phase, and it is then determined from the oxygen content in the air being exhaled by the patient whether a cardiopulmonary resuscitation is being performed on the patient.

In any case, it is achieved in case of these possibilities that the operating method for a ventilation system is designed such that it changes automatically over from the first mode of operation intended for normal ventilation to the second mode of operation intended for cardiopulmonary resuscitation when the presence of resuscitation measures is detected.

In another embodiment, the method according to the present invention may be carried out with a ventilation system that has a display unit, wherein a first alarm message is generated on the display unit in the first mode of operation when a parameter detected by the sensor unit exceeds or falls below a threshold value, and no alarm message is generated or a second alarm message differing from the first alarm message is generated in the second mode of operation when the parameter detected by the sensor unit exceeds or falls below the threshold value. In particular, the display unit may have acoustic signal device for generating an acoustic alarm, the first alarm message comprising a first acoustic alarm and the second alarm message comprising no acoustic alarm or comprising a second acoustic alarm, which is different from the first one and whose volume is reduced compared to the first acoustic alarm. It is achieved in this embodiment of the method according to the present invention that when the second mode of operation intended for a cardiopulmonary resuscitation is selected, a user is no longer confronted with alarm messages for which the necessary measures had already been taken by initiating the cardiopulmonary resuscitation. The alarm messages are consequently adapted in this embodiment of the method automatically to the changed situation caused by the cardiopulmonary resuscitation in order to relieve the user of the burden of having to bother about alarms whose cause is already being dealt with actively.

Furthermore, the method according to the present invention may be designed such that a parameter detected by the sensor unit is monitored in the second mode of operation and a first message is generated by the display unit when the parameter falls below a first threshold value, a second message is generated by the display unit when the parameter exceeds the first threshold value and falls below a second threshold value that is higher than the first threshold value, and a third message is generated by the display unity when the parameter exceeds the second threshold value, the first, second and third messages being different from one another.

In particular, the ventilation system may be designed in this embodiment of the method such that the sensor unit has a sensor, which is designed to determine the $CO_2$ content in the air being exhaled by the patient during the expiration phase, the $CO_2$ content in the air being exhaled by the patient being the monitored parameter. As an alternative, the ventilation system may also have a sensor for measuring the oxygen saturation in the blood ($SPO_2$), which may be connected to a patient, in which case the oxygen saturation in the blood ($SPO_2$) is the monitored parameter.

When the method is taking place according to this embodiment and the first and second threshold values are set properly, a feedback can be given to a user during the performance of a cardiopulmonary resuscitation on whether the cardiopulmonary resuscitation is being carried out correctly and whether this must be continued. If, for example, the $CO_2$ content in the air being exhaled by the patient is used as the monitored parameter, the first message shows that the desired effect is not achieved despite the performance of a cardiopulmonary resuscitation, so that the performance of the resuscitation measures should be checked. When the second message is generated, the $CO_2$ content is between the two threshold values, which shows that the cardiopulmonary resuscitation is being carried out in such a manner that a sufficient supply is ensured for the organs. Finally, the third message, which is generated when the $CO_2$ content in the breathing air is above the second threshold value, shows that the patient can breathe on his own and the cardiopulmonary resuscitation does not have to be continued.

Finally, the method may also be carried out together with a ventilation system that has a device for automatically performing a cardiopulmonary resuscitation, in which case a switch over is performed from the first to the second mode of operation when the device for performing a cardiopulmonary resuscitation is activated.

A ventilator according to the present invention is designed for performing the method according to the present invention for operating a ventilator which assists cardiopulmonary resuscitation (CPR).

Such a ventilator comprises for this actuators and sensors with corresponding control elements, which are designed in practice as a central or non-central control and regulation unit, as well as a display, signal generation and operating unit. Additional data inputs and outputs, sensor system or data interfaces, which make it possible to exchange data with other devices or accessory components, may optionally be provided on this ventilator.

Such a ventilator may be designed in a special embodiment as a so-called emergency ventilator, a device designed especially for ventilation in emergency situations, for example, in the form of a mobile, portable device, which can be operated independently from a power supply voltage and a gas supply. The independence of the emergency ventilator from the power supply voltage is achieved by the device being equipped with batteries, for example, rechargeable batteries or primary batteries.

The independence of the emergency ventilator from the gas supply can be achieved by carrying gas or a plurality of gases in pressurized gas cylinders, optionally combined with a design with a blower as the ventilation drive for providing air as a breathing gas. A nozzle arrangement drawing in ambient air, a so-called ejector, usually designed in the technical embodiment as a so-called Venturi nozzle, combined with a pressurized oxygen gas source, usually designed as a pressurized oxygen cylinder, may be used to mix and meter the gases, essentially to mix air and oxygen. A blower drive, embodied technically as a radial compressor or as a side channel blower in conjunction with metering valves for metering and mixing the gases, may be used as an alternative hereto. The additional components of the ventilator necessary for performing and controlling the ventilation of a patient, besides gas supply and electric power supply, include an inspiratory metering unit designed to be suitable for metering, usually designed as or comprising at least one inspiration valve or an array of a plurality of valves or valve elements for metering and mixing the quantity of air and the quantity of gas and for setting the patient's airway pressure during the inspiration phases of the patient. Furthermore, the additional necessary components of the ventilator include an expiratory metering unit, designed, for example, as an expiration valve whose degree of opening is controllable for setting the inspiration and expiration phases, as well as for setting the patient's airway pressure, the expiration valve may be able to be designed as an internal valve in the ventilator or as an external expiration valve arranged in the gas supply to the patient.

Additional components of the ventilator according to the present invention are sensors for pressure measurements, which are suitable for performing a pressure measurement and pressure regulation in conjunction with the control and regulation unit during inspiration and/or expiration. Furthermore, sensors for inspiratory/expiratory flow measurement are preferably components of the ventilator, which are preferably suitable for performing a preferred flow measurement, flow rate measurement and/or flow regulation in conjunction with the control and regulation unit. An additional sensor system, which is designed to monitor the metering and mixing of the gases in conjunction with the control and regulation unit, is preferably additionally present. The pressure measurement is used here to detect a current ventilation pressure and a curve of the ventilation pressure, which is supplied to the patient during the inspiration phase, and the current ventilation pressure, which remains as a positive end-expiratory pressure (PEEP) at the end of the expiration in the patient's lungs. Furthermore, the ventilation pressure is used as the actual value when pressure-controlled ventilation is performed. For example, CPAP (Continuous Positive Airway Pressure), PC-BiPAP (Bi-level Positive Airway Pressure), PC-AC (Pressure Control-Assist Control), PC-PSV (Pressure Control-Pressure Support Ventilation) are available as possible pressure-controlled forms of ventilation.

The flow rate determined by means of the preferred flow measurement is used here to detect the actual flow and the curve of the flow rate during the ventilation. By integrating the current flow values or the curve of the flow rate, the volume is determined from the flow rate. It is possible as a result both to determine the patient's applied respiratory minute volume (RMV) and to recognize possible leaks in the air supply to the patient by balancing the inspiration and expiration volumes. Furthermore, the flow rate or the volume determined therefrom is used as an actual value when performing a volume-controlled ventilation. For example, VC-SIMV (Volume Control-Synchronized Intermittent Volume Control), VC-MMV (Volume Control-Mandatory Minute Volume), VC-CMV (Volume Control-Continuous Mandatory Ventilation) are available as possible volume-controlled forms of ventilation. This list of the forms of ventilation is only an example at this point and in no way complete and final. In addition, the pressure measurement and the flow measurement during the ventilation make possible the chronologically current monitoring of maximum limits of the ventilation pressure and flow, which should not be exceeded in order to ensure safe ventilation. Additional components are an input unit for inputting parameters, an output unit, for example, in the form of a display screen for outputting operation and status parameters as well as measured values, as well as for displaying curves and for providing information to the user. In addition, a sensor or data interface is provided for exchanging data with external devices, with external physiological monitoring devices (physiological monitoring device) or for signal and data exchange with accessories or sensor systems belonging or assigned to the device or additional accessories or sensor systems and, possibly also via the intermediary of additional components for adapting the protocol and levels, for communication in a data network (intranet, LAN, WLAN, internet). Furthermore, a control and regulation unit is provided for detecting and processing measured values (flow measurement, pressure measurement), for polling the input unit, controlling the output unit and for the general control of the emergency ventilator, as well as especially for controlling the ventilation with different modes of operation of ventilation and different forms of ventilation (modes of ventilation). The parameters transmitted via the input unit for controlling the ventilation arise from the diagnostic marginal conditions and the therapeutic considerations of the user, taking the constitution (gender, age, body weight, height, diagnosis) of the patient into account, and they yield specifications for the operation of the ventilator which assists cardiopulmonary resuscitation (CPR). The respiration rate (RR), the target pressure of ventilation (P), the maximum pressure amplitude during ventilation, the tidal volume (Vt) and the I:E ratio, which corresponds to the ratio of the duration of inspiration to the duration of expiration, are sent as parameters for controlling and regulating the ventilator which assists cardiopulmonary resuscitation to a control and regulation unit. On the one hand, these parameters can be set by the user as direct set values on a control unit, and the set values may also be derived from other parameters in another variant. Furthermore, an alarm and alarm adaptation unit is present for monitoring threshold values and tolerance ranges, in which corresponding threshold values and one or more tolerance ranges, which are independent or are in a relation to one another, are preset or set by the user, at times after presetting (default settings) or after derivation from the parameters, and they are then set by the user definitively and finally by acknowledgment/confirmation. Acoustic and/or optical alarms are triggered on the ventilator when values exceed or fall below the threshold values or if a value leaves one or more tolerance ranges. Such an alarm and alarm adaptation unit is closely connected to the display and signal generation unit, the input unit and the control and regulation unit or is at least partially integrated in it.

A patient is connected to the ventilator and is supplied with breathing gas via a tube system. The tube system comprises an inspiratory branch for supplying air and fresh breathing gas from the ventilator to the patient and an expiratory branch for moving spent breathing gas from the patient to the ventilator. The patient is connected to the ventilator via the tube system via a connection piece, preferably a Y-piece for connecting the inspiratory branch and the expiratory branch.

The control and regulation unit converts the parameters into the necessary manipulated variables for the pressure and flow regulation and the actuation of the components of the device, for example, the actuators. At least one inspiratory metering unit, designed, for example, as an inspiratory metering valve (inspiration valve) and/or ventilation drive or as a radial compressor, as well as an expiratory metering unit, designed, for example, as an expiratory metering valve (expiration valve), are present as actuators in the ventilator. Furthermore, the sensor systems present in the ventilator include at least one pressure sensor. The at least one pressure sensor is preferably arranged as an inspiratory pressure sensor in the inspiratory branch of the ventilator or as an expiratory pressure sensor in the expiratory branch of the ventilator. An additional pressure sensor is also preferably present in the ventilator. At least one flow sensor, preferably designed in the form of an inspiratory and/or expiratory flow sensor and/or in the form of a flow sensor located close to the patient, is also preferably present in the ventilator. Due to the conversion of the manipulated variables into the actuation of the actuators, especially of the inspiratory and expiratory metering unit, and the inclusion of the sensor system, especially of the inspiratory pressure sensor, and also preferably of the expiratory pressure sensor, and also preferably of the inspiratory and/or expiratory flow sensor and/or of the flow sensor located close to the patient, the control and regulation unit is able to carry out the ventilation of the patient according to the settings and the specifications of the user and to monitor compliance with the specifications and settings. Two fundamentally different tube systems are commonly used in clinical practice. There are so-called "one-tube systems" as well as so-called "two-tube systems." A "one-tube system" is preferably used on emergency ventilators and is characterized in that a single tube, which delivers an inspiratory air/gas mixture to the patient during inhalation, is led from the ventilator to the patient. The expiratory metering valve, via which the air being exhaled by the patient escapes into the surrounding area, is provided on the connection piece to the patient on the "one-tube system." This metering valve is also frequently called "expiration valve located close to the patient" in case of embodiment in a "one-tube system." Furthermore, the expiratory pressure sensor is arranged in the connection piece. A "two-tube system" is characterized in that two tubes are led from the ventilator to the patient, a first tube delivering the inspiratory air/gas mixture to the patient during inhalation and a second tube returning the exhaled air to the ventilator. The expiratory metering valve as well as the expiratory pressure sensor are arranged in the expiratory branch in the ventilator. It is common to both tube systems that the expiratory metering valve and the expiratory pressure sensor are arranged close to one another. Therefore, this is especially advantageous because the adjusting element for setting the ventilation pressure and the measuring element for detecting the ventilation pressure can act in a ventilation pressure control circuit without an essential offset in time in relation to one another. It is possible, in principle, in a "two-tube system" that an additional pressure sensor is provided on the connection piece in order to further optimize the ventilation pressure control circuit and to make it possible, for example, to compensate differences in the length of the ventilation tubes, water traps or breathing air humidifiers.

A device according to the present invention is designed especially as a medical ventilator and comprises the following components, which are necessary as a minimum for the operation of the ventilator which assists cardiopulmonary resuscitation (CPR) and for ventilating a patient:

An inspiratory metering unit, an expiratory metering unit, a control and regulation unit, an alarm and alarm adaptation unit, a display, signal generation and operating unit for outputting display values, alarms and signals to a user and for inputting setting values by the user, at least one pressure sensor for monitoring threshold values, and a sensor or data interface for connecting sensors or external devices or physiological monitoring devices. The control and regulation unit is designed in this device according to the present invention to continuously detect a current value of a pressure of the at least one pressure sensor, to compare the current value of a pressure with a first predetermined value and to actuate the expiratory metering unit such that the current value of the pressure corresponds to the first predetermined value. The patient is preferably and usually connected to the medical ventilator by means of a tube system.

In a first embodiment of the device according to the present invention, the control and regulation unit is designed to actuate the expiratory metering unit and the inspiratory metering unit such that the current value of the pressure is increased during a first phase by a second predetermined value relative to a first predetermined value, and to actuate the expiratory metering unit and the expiratory metering unit such that the current value of the pressure is reduced relative to the first predetermined value by a third predetermined value during a second phase.

In a second embodiment of the device according to the present invention, at least one additional sensor is present in addition to the at least one pressure sensor, and the control and regulation unit is designed to receive a signal of the at least one sensor or of the at least one pressure sensor and to analyze the signal of the at least one sensor or pressure sensor and/or the time curves of the signals of the at least one sensor or of the at least one pressure sensor, and to determine at least one sign (CM) activity to determine whether a cardiac massage is being performed on the patient.

In another preferred embodiment of the second embodiment of the device according to the present invention, the control and regulation unit is designed to analyze the signal of the at least one sensor and/or the time curve of the signal and/or the signal of the at least one pressure sensor and/or the time curve of the signal of the at least one pressure sensor to determine a quality index (QIndex-CM) concerning the quality with which a cardiac massage is performed. The quality index (QIndex-CM) may preferably be determined by a comparison of an actually detected signal of the at least one sensor with at least one predetermined quality threshold value.

In another preferred variant of the second embodiment of the invention, the device is designed, based on a configuration of the control and regulation unit, to analyze the signal of the at least one pressure sensor and/or from the time curve of the signal of the at least one pressure sensor as a ventilation pressure and/or time curve of the ventilation pressure such that a cardiac massage (CM) currently being applied is recognized and an operation of the ventilator which assists cardiopulmonary resuscitation (CPR) is automatically started.

In another preferred variant of the second embodiment, the device is designed to analyze the ventilation pressure and/or the curve of the ventilation pressure such that a current ending of a previously applied cardiac massage (CM) is recognized and the operation of the ventilator which assists cardiopulmonary resuscitation (CPR) is ended.

The at least one additional sensor is also designed preferably as at least one physiological sensor. The at least one physiological sensor is preferably designed as a sensor for detecting a carbon dioxide concentration ($CO_2$) in the breathing gas of a patient. The at least one physiological sensor is also preferably designed as a sensor for determining an oxygen saturation ($SPO_2$) in the blood of a patient.

The at least one additional sensor is preferably designed here as at least one flow sensor. The at least one flow sensor is also preferably designed as an inspiratory flow sensor, expiratory flow sensor or as a flow sensor located close to the patient.

In an special variant of the second embodiment of the device according to the present invention, the device is designed by means of the control and regulation unit to analyze the signal of the at least one physiological sensor and/or a time curve of the signal of the at least one physiological sensor in order to determine the at least one quality index (QIndex-CM) concerning the performance of the cardiac massage (CM).

In a special variant of the second embodiment of the device according to the present invention, the device is designed by means of the control and regulation unit to use a signal of at least one physiological sensor and/or a time curve of the signal of the at least one physiological sensor and/or the signal of the at least one pressure sensor as a ventilation pressure and/or the time curve of the signal of the at least one pressure sensor as the curve of the ventilation pressure in order to determine the at least one sign (CM activity) that a cardiac massage is currently being performed and/or to determine the at least one quality index (QIndex-CM) concerning the performance of the cardiac massage (CM).

In another variant of the second embodiment of the device according to the present invention, the device is designed by means of the control and regulation unit in conjunction with the at least one flow sensor designed as an expiratory flow sensor, inspiratory flow sensor or flow sensor located close to the patient to use signals of the at least one flow sensor and/or the time curves of the signals of the at least one flow sensor in order to determine the at least one sign (CM activity) whether a cardiac massage (CM) is being performed on the patient and/or to determine the at least one quality index (QIndex-CM) concerning the performance of the cardiac massage (CM).

The physiological sensor according to the likewise preferred embodiment of the second embodiment of the device according to the present invention is designed to detect at least one physiological signal as a parameter relevant for the cardiopulmonary resuscitation (CPR). If the physiological sensor is used as a sensor to determine the at least one sign (CM activity) to determine whether a cardiac massage is being performed on the patient, and/or to determine the at least one quality index (QIndex-CM) concerning the quality with which the cardiac massage is performed, the term physiological sensor is defined in the sense of another preferred embodiment of the second embodiment of the device according to the present invention as and also comprises any type of sensor system that provides information concerning the patient's status. The physiological sensor system is characterized in the sense of the present invention in that measured physiological variables and signals of the device according to the present invention are made available. Contrary to this, an operating sensor system in the sense of the present invention is characterized in that it detects status variables on the operating state of the medical ventilator or on the course of the operation during ventilation, e.g., flow rates, temperatures, pressure values. The following list of different physiological sensors and physiological parameters is by no means complete and final in the sense of the present invention. Physiological parameters detectable by means of physiological sensors in the sense of the present invention for use to determine the quality index (QIndex-CM) of the cardiac massage and/or to determine a sign (CM activity) to determine whether and how a cardiac massage is being performed and/or for an analysis at the start or at the end of the operation of a ventilator which assists cardiopulmonary resuscitation (CPR) are essentially:

a carbon dioxide concentration in the breathing gas ($CO_2$) of the patient, an oxygen saturation in the blood ($SPO_2$) of the patient.

The physiological sensor is designed in a preferred manner in this additional preferred embodiment of the second embodiment as a sensor or as an external physiological monitoring device (capnometer) to detect the concentration of carbon dioxide in the gas being exhaled by the patient. In a first variant, the carbon dioxide concentration ($CO_2$) in the air being exhaled by the patient is detected and measured by a defined quantity of air being delivered continuously from the connection piece via a suction line to the external physiological monitoring device and/or to the physiological sensor and being analyzed in the external physiological monitoring device and/or the physiological sensor. This measurement method is called "sidestream measurement," and sensors designed suitably for this are called "$CO_2$ sidestream sensors." In a second variant of the detection and measurement of the carbon dioxide concentration ($CO_2$) in the air being exhaled by the patient, the detection of the carbon dioxide concentration ($CO_2$) is performed continuously with a physiological sensor at the connection piece. The physiological sensor preferably operates in the usual embodiment according to an infrared optical measurement method in a transmitted light operation directly at the connection piece in the path of the gas to the patient. This measurement method is called "$CO_2$ mainstream measurement" and a sensor designed suitably for this is called a $CO_2$ mainstream sensor."

The physiological sensor at the connection piece may also contain at the connection piece in a technical embodiment the components necessary for the measurement, analysis and determination of the carbon dioxide concentration ($CO_2$) as well as for the display thereof, but in another type of technical embodiment, the components for the analysis, determination and display of the carbon dioxide concentration ($CO_2$) may also be arranged in an eternal physiological monitoring device, which is connected to the physiological sensor by means of a data and/or energy link. A flow sensor located close to the patient is preferably arranged in this variant at the connection piece to the patient to balance the inhalation and exhalation volume flows and—by means of integration over time—to balance inhalation and exhalation volumes.

In another preferred form of the additional variant of the second embodiment of the device according to the present invention, the device is designed (configured), by means of the control and regulation unit, to derive further variables to determine the at least one indication (CM activity) to determine that a cardiac massage is currently being performed, as well as to determine the at least one quality index (QIndex-CM) concerning the performance of the cardiac massage (CM), from the signals and/or signal curves of the inspiratory and/or expiratory flow sensor, as well as from the signals of the physiological sensor and/or from the time curve of the signal of the at least one physiological sensor. Such a derived variable is, for example, an expiratory volume or a minute volume of carbon dioxide ($MVCO_2$), determined from measured values of the flow sensor located close to the patient in conjunction with the measured values of the sensor for detecting a carbon dioxide concentration ($CO_2$) in the breathing gas, which is preferably designed for this as a "$CO_2$ mainstream sensor."

The physiological sensor is designed for this as a sensor for detecting a carbon dioxide concentration ($CO_2$) in the breathing gas. This minute volume of carbon dioxide ($MVCO_2$) can be determined by means of an integration over time of volume flows detected by means of the volume flow sensors in conjunction with the sensor for detecting a carbon dioxide concentration in the breathing gas.

In this additional preferred embodiment, the physiological sensor is preferably designed as a sensor or as an external physiological monitoring device (pulse oximeter) for detecting and determining the oxygen saturation ($SPO_2$) in the blood of the patient.

The oxygen saturation ($SPO_2$) in the blood is preferably detected and measured non-invasively in clinical practice by means of an optical/infrared-optical measurement method, the so-called pulse oximetry in the transmitted-light method, for example, on the finger, toe or earlobe of the patient.

By means of the carbon dioxide concentration ($CO_2$) in the breathing gas and/or the oxygen saturation ($SPO_2$) in the blood, the device according to the present invention is preferably able to determine at each time in what manner a cardiopulmonary resuscitation (CPR) being currently performed is taking place for the patient and/or whether it is effective.

Additional physiological parameters in the sense of the present invention are:

an oxygen concentration (O2) in the breathing gas of the patient, a carbon dioxide partial pressure (CO2) in the blood of the patient, an oxygen partial pressure in/under the cutaneous tissue (transcutaneously) of the patient, a carbon dioxide partial pressure in the cutaneous tissue (transcutaneously) of the patient, an oxygen concentration (O2) having average activity in the patient's lungs, a diastolic blood pressure value of the patient determined invasively or non-invasively, a systolic blood pressure value of the patient determined invasively or non-invasively, invasively detected blood gas values of the patient (on-site blood gas analysis), a heart beat or a pulse rate of the patient, a cardiological signal, e.g., ECG signals, EEG signals, EMG signals, a sonographic signal, for example, of a blood vessel of the patient, and a tomographic signal, for example, of the lungs of the patient.

Furthermore, variables derived from the above-mentioned physiological variables as well as variables that are derived from the latter and/or combined with one another are also covered in the sense of the present invention. The physiological sensor is preferably connected directly to the device according to the present invention by means of the sensor and data interface.

In another preferred variant, the physiological sensor is connected to an external device, which is connected to the device according to the present invention by means of the sensor and data interface. The data and/or measured values of the physiological sensor connected to the external device are transmitted via the sensor and data interface to the device according to the present invention.

The quality index (QIndex-CM) of the performance of the cardiac massage may be determined here in a suitable manner by a comparison of a currently detected signal of the physiological sensor with at least one predetermined quality threshold value. In an embodiment of the physiological sensor as a sensor for detecting the carbon dioxide concentration in the breathing gas, a carbon dioxide concentration of, for example, of 10 mmHg with a variation of +/−2 mmHg is a value suitable for the determination of the quality index (QIndex-CM) for practical use in emergency medicine as a predetermined quality threshold value. A value above 10 mmHg corresponds here to the performance of a cardiac massage being performed properly for resuscitating the patient.

In one embodiment of the physiological sensor as a sensor for detecting and determining the oxygen saturation ($SPO_2$) in the blood of the patient, a value above 70% with a variation of +/−10% is a value suitable for the determination of the quality index (QIndex-CM) for practical use in emergency medicine as a predetermined quality threshold value.

In another preferred variant of the second embodiment of the device according to the present invention, the device is designed by means of the alarm and alarm adaptation unit in conjunction with the display and signal generation unit to send a message to the user when an actual value falls below a first predetermined threshold value of the signal of the physiological sensor, indicating that a changeover to the operation of the ventilator with assisted cardiopulmonary resuscitation (CPR) is recommended for the current situation of the patient, and an input is to be expected from the user to start the operation of the ventilator with assisted cardiopulmonary resuscitation (CPR). Furthermore, the message to the user may preferably contain an instruction that the user shall perform cardiopulmonary resuscitation (CPR) with cardiac massage on the patient in the patient's current situation.

In another preferred embodiment of the second embodiment, the device is designed by means of the control and regulation unit to analyze the signal of the physiological sensor such that the method for operating a ventilator with assisted cardiopulmonary resuscitation (CPR) will be started.

In another preferred embodiment of the second embodiment, the device is designed by means of the control and regulation unit to analyze the signal of the physiological sensor such that the method for operating a ventilator with assisted cardiopulmonary resuscitation (CPR) will be ended.

The device is designed in a special variant of the second embodiment to start the operation of the ventilator with assisted cardiopulmonary resuscitation (CPR) automatically, i.e., automatically, preferably without a further user interaction, besides the above-mentioned message to the user, when an actual value falls below the first predetermined threshold value of the signal of the physiological sensor.

In one embodiment of the physiological sensor as a sensor for detecting the carbon dioxide concentration in the breathing gas, a value of, for example, 20 mmHg with a variation of +/−2 mmHg is a value suitable for automatically starting the operation of the ventilator with assisted cardiopulmonary resuscitation (CPR) for practical use in emergency medicine as a first predetermined threshold value. If the physiological sensor is designed as a sensor for detecting and determining the oxygen saturation ($SPO_2$) in the blood of the patient, a value of, for example, 60% with a variation of +/−5% is a value suitable for automatically starting the operation of the ventilator with assisted cardiopulmonary resuscitation (CPR) for practical use in emergency medicine as a first predetermined threshold value.

In another preferred variant of the second embodiment, the device is designed by means of the control and regulation unit to analyze the signal of the physiological sensor so as to end the operation of the ventilator with assisted cardiopulmonary resuscitation (CPR) automatically, i.e., automatically, preferably without further user interaction, when an actual value exceeds a second predetermined threshold value.

In an embodiment of the physiological sensor as a carbon dioxide sensor for detecting the carbon dioxide concentration in the breathing gas, a value of, for example, 40 mmHg with a variation of +/−2 mmHg is a value suitable for automatically ending the operation of the ventilator with assisted cardiopulmonary resuscitation (CPR) for practical use in emergency medicine as a second predetermined threshold value.

In an embodiment of the physiological sensor as a sensor for detecting and determining the oxygen saturation ($SPO_2$) in the blood, a value of, for example, 90% with a variation of +/−5% is a value suitable for automatically ending the operation of the ventilator with assisted cardiopulmonary resuscitation (CPR) for practical use in emergency medicine as a second predetermined threshold value.

Indicating the carbon dioxide concentration in the breathing gas as a partial pressure in the "mmHg' unit is common in medical and clinical practice. Indications or conversion forms into other units of pressure (hPa, mbar, $cmH_2O$, as well as indications in concentrations (%) are also covered in an equivalent manner in the sense of the present invention. Indicating the oxygen saturation ($SPO_2$) as a concentration value in (%) is common practice in medical and clinical practice. Indications in other units or conversion forms of the partial pressure (mmHg, hPa, mbar, cmH$_2$O) are also covered in an equivalent manner in the sense of the present invention.

The ventilation pressure or the time curve of the ventilation pressure may be analyzed to recognize a cardiac massage (CM) being currently applied, for example, by means of a comparison of the shape of the curve describing the current changes over time in the ventilation pressure with a usual curve describing the changes in the ventilation pressure. The usual curve of the ventilation pressure is selected either such that the curve is free from additional cyclic rhythmic pressure peaks typical of the effect of the cardiac massage (CM) or such that the curve has cyclic rhythmic additional pressure peaks typical of the effect of the cardiac massage (CM). It is then possible to recognize by a comparison of the curves, for example, by a subtraction with preceding and/or subsequent filtering and standardization, whether or not a cardiac massage (CM) is currently just being performed.

A cardiac massage (CM) being currently applied can be recognized according to the above-described embodiments for recognizing, starting or ending the operation of the ventilator with assisted cardiopulmonary resuscitation (CPR) in such a form that the changes caused by the cardiac massage (CM) currently being applied in the signal and/or in the curve describing the signal of the at least one pressure sensor are determined. The signal or the time curve of the signal of the at least one pressure sensor represents the ventilation pressure and/or the time curve of the ventilation pressure. The changes of the signal or on the time curve of the signal of the at least one pressure sensor are visible and detectable on the curve of the ventilation pressure as increases in amplitude in the chronological rhythm at which the cardiac massage (CM) is carried out. The increase in amplitude for a predetermined minimum duration of the amplitude increase as an absolute minimum duration or as a relative minimum duration in relation to the respiration rate, a predetermined minimum extent of the amplitude increase as an absolute pressure rise or as a relative pressure rise in relation to the curve describing the ventilation pressure, as well as combinations of the above-mentioned amplitude/duration criteria with one another may be used as possible criteria for recognizing a cardiac massage (CM) currently being applied.

Some values is mentioned for this below as an example. The absolute minimum duration of the amplitude increase on the signal of the at least one pressure sensor is obtained as a time of 0.2 sec to 0.5 sec as a range meaningful for clinical practice for recognizing that a cardiac massage (CM) is currently being applied.

In another preferred embodiment of the second embodiment, the device is designed to analyze the signal of the physiological sensor and/or the time curve of the signal of the physiological sensor and/or the signal of the at least one pressure sensor and/or the time curve of the signal of the at least one pressure sensor, to recognize a cardiac massage (CM) currently being applied, and to automatically start the operation of the ventilator with assisted cardiopulmonary resuscitation (CPR).

In another preferred embodiment of the second embodiment of the device according to the present invention, the control and regulation unit is designed to analyze the signal of the physiological sensor and/or of the time curve of the signal of the physiological sensor and/or the signal of the at least one pressure sensor and/or the time curve of the signal of the at least one pressure sensor, to recognize a current ending of a cardiac massage (CM) being applied, and to automatically end the operation of the ventilator with assisted cardiopulmonary resuscitation (CPR).

In another preferred embodiment of the second embodiment of the device according to the present invention, the control and regulation unit is designed to analyze the signal of the physiological sensor and/or the time curve of the signal of the physiological sensor and/or the signal of the at least one pressure sensor and/or the time curve of the signal of the at least one pressure sensor and/or the signal of the at least one flow sensor and/or the time curve of the signal of the at least one flow sensor to determine the at least one sign (CM activity) of whether a cardiac massage is being performed on the patient and/or to determine a quality index (QIndex-CM) concerning the quality with which a cardiac massage is performed.

In another preferred embodiment of the second embodiment, the device is designed to analyze the signal of the physiological sensor and/or the time curve of the signal of the physiological sensor, the signal of the at least one flow sensor and/or the time curve of the signal of the at least one flow sensor and/or the signal of the at least one pressure sensor as a ventilation pressure and/or the time curve of the signal of the at least one pressure sensor as a curve of the ventilation pressure, to recognize a cardiac massage (CM) currently being applied, and to automatically start the operation of the ventilator with assisted cardiopulmonary resuscitation (CPR).

In another preferred embodiment of the second embodiment of the device according to the present invention, the control and regulation unit is designed to analyze the signal of the physiological sensor and/or the time curve of the signal of the physiological sensor, the signal of the at least one flow sensor and/or the time curve of the signal of the at least one flow sensor and/or the signal of the at least one pressure sensor as a ventilation pressure and/or the time curve of the signal of the at least one pressure sensor as a curve of the ventilation pressure, to recognize a current ending of a cardiac massage (CM) being applied, and to automatically end the operation of the ventilator with assisted cardiopulmonary resuscitation (CPR).

In a preferred embodiment of the second embodiment of the device according to the present invention, the alarm and alarm adaptation unit is designed, in conjunction with the display and signal generation unit and the control and regulation unit, to output the at least one sign (CM activity) and/or the at least one quality index (QIndex-CM) to the user.

In a preferred embodiment of the second embodiment of the device according to the present invention, the alarm and alarm adaptation unit is designed, in conjunction with the display and signal generation unit and the control and regulation unit, to analyze the signal of the at least one physiological sensor such that a message is sent to the user when a current value falls below a first predetermined threshold value.

In a preferred embodiment of the second embodiment of the device according to the present invention, the alarm and alarm adaptation unit is designed, in conjunction with the display and signal generation unit and the control and regulation unit, to analyze the signal of the at least one physiological sensor such that a message is sent to the user when a current value exceeds a second predetermined threshold value.

In a preferred embodiment of the first or second embodiment of the device according to the present invention, the alarm and alarm adaptation unit is designed, together with the display and signal generation unit, to change an alarm generation on the ventilator. A preferred change of an alarm generation on the ventilator is to delay or to suppress the generation of at least one alarm for at least one measured value or for at least one measured variable or for at least one event or to vary the volume with which the at least one alarm is generated for the at least one measured value or for the at least one measured variable or for the at least one event. The alarm and alarm adaptation unit is designed in this preferred embodiment of the first or second embodiment of the device according to the present invention to manage and prioritize the alarms and to partially, temporarily or fully suppress the sending of alarm to the user as well as to vary the volume of the alarm. An adaptation of the alarms to the patient's situation is present for this in the alarm and alarm adaptation unit in order to make it possible to adapt, for example, the volume of the acoustic alarms to the situation, especially to increase or decrease it. A periodic, temporary, partial suppression, delay, skipping, fading out or switching off of alarms is defined in the sense of the present invention as any measure and also covers the circumstance that an alarm based on a measured signal, on the fact that a measured value exceeds or falls below a threshold value or based on an event or incident (e.g., an accidental disconnection of a sensor) during the conventional operation and an alarm provided in the course of the ventilation during the operation of the ventilator with assisted cardiopulmonary resuscitation (CPR) is not sent directly to the user. The alarm and alarm adaptation unit is designed such that the type of partial, temporary or full suppression takes place as a function of the current operation of the ventilator (ventilation mode). Additional threshold values and tolerance ranges, for example, ventilation pressure, flow rate, inspiratory and expiratory volumes, respiratory minute volume, are monitored in the alarm and alarm adaptation unit and made available to the user as at least one signal generation, besides the threshold values and tolerance ranges that correspond to the parameters for the control and regulation of ventilation and are derived therefrom, for monitoring measured values and for monitoring measured values and measured variables derived from measured values. An at least one signal generation is defined in the sense of the present invention such that an alarm signal is generated optically or acoustically, optically and acoustically simultaneously or with a time offset and/or that a further or additional external signal generation is carried out by the alarm being available in the form of an electric signal on an analog or digital, wired or telemetric data interface.

In another preferred variant of the first or second embodiment of the device according to the present invention, the alarm and alarm adaptation unit is designed, in conjunction with the control and regulation unit, to change the alarm limits that are active and relevant during the operation of the ventilator with assisted cardiopulmonary resuscitation (CPR) on the basis of the alarm limits set originally during the operation of the ventilator with assisted cardiopulmonary resuscitation (CPR). The alarm limits set originally were set, for example, by the user before the start of the operation of the ventilator with assisted cardiopulmonary resuscitation (CPR). The change of the alarm limits caused, in a further preferred and suitable manner, that an alarm is not sent to the user for at least one measured value, for at least one measured variable or for at least one event.

The alarm and alarm adaptation unit also preferably uses for this the amplitude increases in the chronological rhythm at which the cardiac massage (CM) is performed on the signal of the at least one pressure sensor or on the time curve of that signal to change the alarm limits for the recognition of the performance of the cardiac massage (CM).

The list in the following table contains some exemplary alarm limits and measured variables:

| | |
|---|---|
| RMV-High | A target value of the respiratory minute volume preset by the user is exceeded |
| RMV-Low | A target value of the respiratory minute volume preset by the use is not reached |
| Paw-High | A target value of the maximum ventilation pressure preset by the user is exceeded |
| etCO$_2$-Low | A target value of the end-tidal carbon dioxide concentration (CO$_2$) preset by the user is not reached |
| etCO$_2$-High | A target value of the end-tidal carbon dioxide concentration (CO$_2$) preset by the user is exceeded |
| F$_{spon}$-High | A limit value of a spontaneous respiration rate preset by the user is exceeded |
| PEEP-Low | A limit value of a positive end-expiratory pressure (PEEP) preset by the user is not reached |
| Pressure Limited | The ventilator regulates to a pressure limitation |
| V$_T$-not-reached | A desired value of a tidal volume (V$_T$) preset by the user is not reached |

The method according to the present invention for assisting cardiopulmonary resuscitation (CPR) and the device according to the present invention for carrying out the method for operating a ventilator which assists cardiopulmonary resuscitation (CPR) make it possible to ventilate a patient under the influence of the simultaneous effect of a cardiac massage (CM) on the detection of the ventilation pressure. The technical effect of the cardiac massage (CM) applied from the outside on the ventilator and on the operation and on the guarantee of the operational safety corresponds to a modulation of an interference variable on the control circuit for controlling the ventilation pressure during the ventilation.

It is ensured according to the present invention that, on the one hand, a regulated ventilation that is advantageous for the patient is guaranteed during simultaneous compression of the chest cavity and, on the other hand, that the ventilation is carried out in such a way that the inflow and outflow of blood to the heart due to the cardiac massage (CM) is not adversely affected by the ventilation.

The method according to the present invention for operating a ventilator which assists cardiopulmonary resuscitation (CPR) and the device according to the present invention for carrying out the method for operating a ventilator which assists cardiopulmonary resuscitation (CPR) make it possible both that the ventilation by the ventilator brings about an efficient exchange of air in the patient's lungs and can be carried out efficiently during cardiac massage (CM) and that the efficiency of the cardiac massage (CM) with an efficient exchange of blood from the heart into the patient's body is not adversely affected by the ventilation and the patient will thus return as a result into a stable state with spontaneous cardiovascular function after a relatively short duration of the cardiopulmonary resuscitation (CPR).

The application of the method according to the present invention to assist cardiopulmonary resuscitation (CPR) causes that at the end of the inspiration and before the start of expiration by the patient, a volume, which is larger than the volume which would fill the patient's lungs at the end of the inspiration with the application of a ventilation with a normal ventilation mode, i.e., with a mode of ventilation without assisted cardiopulmonary resuscitation (CPR), will fill the patient's lungs, so that the lungs fill a part of the chest cavity and thus the possibility that the heart would yield in the chest cavity during compression by the cardiac massage (CM) is reduced and the best possible delivery of the blood from the heart to the body parts, especially to the brain, is thus brought about by the compression.

The application of the method according to the present invention of assisting cardiopulmonary resuscitation (CPR) causes that at the end of the expiration and before the start of the inspiration by the patient, the lungs are filled essentially only with a volume that corresponds essentially only to the volume of the functional residual capacity, so that a reduced residual volume will remain in the lungs compared to the case of ventilation with a normal mode of ventilation, without assistance of cardiopulmonary resuscitation (CPR), so that the backflow of the blood from the body to the heart is assisted during the decompression of the chest cavity.

In one embodiment according to the present invention of the method for assisting cardiopulmonary resuscitation (CPR), a ventilator is operated according to the present invention according to a method for operation with mandatory ventilation of a patient and with assisted cardiopulmonary resuscitation (CPR). The ventilator comprises here an expiration valve, a pressure sensor, a ventilation drive and a control and regulation unit.

It is advantageous for an optimal regulation of the ventilation pressure that is comfortable for the patient that pneumatic effects, for example, pressure changes brought about by an adjustment of the degree of opening of the expiration valve, can be detected by the pressure sensor in as timely a manner as possible and effects due to propagation paths and propagation times of pressure changes based on gas species-specific sound velocities are more or less negligible. The pressure sensor is therefore preferably arranged on or in the immediate vicinity of the expiration valve.

If a pneumatic connection of the ventilator is established with a so-called "two-tube system," the pressure sensor and the expiration valve are arranged close to one another in the ventilator itself. If a pneumatic connection of the ventilator is established with a so-called "one-tube system," the pressure sensor and the expiration valve are arranged close to one another on the connection piece, the so-called "Y-piece" to the patient.

The method for operating the ventilator which assists cardiopulmonary resuscitation (CPR) is designed as a continuously repeating sequence of at least two phases of a ventilation. The at least two phases are designed as a first phase and a second phase. In this operation of the ventilator with assisted cardiopulmonary resuscitation (CPR), a current value of a pressure is continuously determined. This current value of a pressure is representative of a current airway pressure of the patient. The current pressure value determined is continuously compared with a first predetermined value in the control and regulation unit. The control and regulation unit controls the inspiration valve and/or the expiration valve on the basis of the result of the comparison such that the deviation between the first predetermined value and the current pressure value is minimized, so that the current pressure valve corresponds to the first predetermined pressure value. A slight deviation between the first predetermined pressure value and the current pressure value arises from the residual deviation due to technical causes in a control circuit, such as those that are always present in all technical regulating units for a functional regulation.

An initial pressure is increased relative to the first predetermined value by the end of the first phase by a second predetermined value in the first phase of the at least two phases of ventilation.

A pressure increase in the range of 5 hPa to 10 hPa is obtained as a meaningful range for practice for the second predetermined value.

An initial pressure is reduced relative to the first predetermined value at the start of the second phase by a third predetermined value in the second phase of the at least two phases of ventilation.

A pressure reduction in the range of 2 hPa to 5 hPa is obtained as a meaningful range for practice for the third predetermined value.

In a preferred embodiment, the first phase of the ventilation corresponds at least partially to an expiration phase of the patient and the second phase of the ventilation corresponds at least partially to the inspiration phase of the patient.

In another preferred embodiment of the method for operating a ventilator which assists cardiopulmonary resuscitation (CPR), provisions are made for the at least two phases of ventilation to form altogether four partial phases of ventilation, the first phase of the ventilation being divided into a first partial phase and a second partial phase, the first partial phase of the ventilation taking place in time before the second partial phase of the ventilation, and the second phase of the ventilation being divided into a third partial phase of the ventilation and a fourth partial phase of the ventilation, and the third partial phase of the ventilation taking place before the fourth partial phase of the ventilation.

In a special variant, the initial pressure is increased by a second predetermined value relative to the first predetermined value in the first partial phase of the ventilation, and the initial pressure is reduced by a third predetermined value relative to the first predetermined value in the third partial phase of the ventilation.

In another embodiment of the method for operating a ventilator which assists cardiopulmonary resuscitation (CPR), an increase in the initial expiratory pressure level and hence an increase in the air-filled volume of the patient's lungs is brought about by increasing the ventilation pressure at the start of the expiration phase by a desired pressure value being briefly increased in the pressure control circuit of the mechanical ventilation. As a result, the air-filled lungs fill a part of the chest cavity and thus reduce the possibility for the heart to yield in the chest cavity during a compression by the cardiac massage (CM) during the performance of the method for operating a ventilator with assisted cardiopulmonary resuscitation (CPR). This supports the efficiency of the cardiac massage (CM).

The increase in the initial expiratory pressure level is achieved by a time delay with which the expiration valve opens at the start of the expiration phase in another preferred variant. This delay of the opening of the expiration valve at the start of the expiration phase corresponds to a prolongation of the inspiration phase.

In an especially preferred variant, the desired pressure value is briefly increased by the ventilation control in the pressure control circuit of the mechanical ventilation and the expiration valve is additionally opened with a delay, so that there will be a greater increase in the initial expiratory pressure level at the start of the expiration phase.

In another preferred embodiment of the method for operating a ventilator which assists cardiopulmonary resuscitation (CPR), a reduction of an initial inspiratory pressure level in the patient's lungs and the generation of a slight vacuum in the lungs in relation to the ambient pressure is achieved by the supply of fresh breathing air being delayed in time at the beginning of the inspiration phase by delaying the opening of the inspiration valve. The pressure in the chest cavity is thus reduced when the method for operating a ventilator with assisted cardiopulmonary resuscitation (CPR) is carried out, so that the backflow of the blood from the body to the heart during the decompression of the chest cavity is assisted.

In another preferred embodiment of the method for operating a ventilator which assists cardiopulmonary resuscitation (CPR), the operation of the ventilator with assisted cardiopulmonary resuscitation (CPR) is switched on and/or off by an activating device. Such an activating device is preferably designed as a control element or switching element of the ventilator. The user is enabled by means of this control element or switching element to change over directly into the operation of the ventilator with assisted cardiopulmonary resuscitation (CPR) from any other operation of the ventilator, for example, a pressure-controlled or volume-controlled operation without assisted cardiopulmonary resuscitation (CPR), as well as directly into another operation from the operation of the ventilator with assisted cardiopulmonary resuscitation (CPR).

Such a control element or switching element is preferably designed as a part of the input unit, and such a control element is more preferably arranged on the front side in the direct working range and range of access of the user.

In another preferred embodiment of the method for operating a ventilator which assists cardiopulmonary resuscitation (CPR), the operation of the ventilator with assisted cardiopulmonary resuscitation (CPR) is switched on and/or off by an external signal. The external signal is preferably connected electrically, optically or telemetrically to the ventilator by means of the data interchange.

In an especially preferred embodiment of the method for operating a ventilator which assists cardiopulmonary resuscitation (CPR), at least one physiological signal is analyzed as a parameter relevant for the cardiopulmonary resuscitation (CPR). Such relevant parameters are preferably a current oxygen saturation ($SPO_2$) in the patient's blood, an oxygen concentration ($O_2$) in the lungs or in the air exhaled by the patient or a carbon dioxide concentration ($CO_2$) in the air exhaled by the patient.

In a preferred embodiment variant of this especially preferred embodiment (HG1), the method for operating a ventilator which assists cardiopulmonary resuscitation (CPR) is designed to determine a quality index (QIndex-CM) for the performance of the cardiac massage (CM) from the at least one physiological signal. The quality index (QIndex-CM) is preferably determined by means of a comparison of the signal of the at least one physiological signal with a predetermined comparison value or from the fact that a predetermined threshold value is exceeded or not reached.

In another variant of this especially preferred embodiment (HG2) of the method for operating a ventilator which assists cardiopulmonary resuscitation (CPR), the at least one physiological signal is analyzed to automatically start and/or end the operation of the ventilator with assisted cardiopulmonary resuscitation (CPR).

In a special variant of this especially preferred embodiment (HG3) of the method for operating a ventilator which assists cardiopulmonary resuscitation (CPR), a ventilation pressure and/or a time curve of the ventilation pressure are analyzed to recognize a cardiac massage (CM) currently being applied and to automatically start the operation of the ventilator with assisted cardiopulmonary resuscitation (CPR).

In another preferred embodiment of the method for operating a ventilator which assists cardiopulmonary resuscitation (CPR), the alarm generation of the ventilator is also preferably adapted to the effect of the cardiac massage (CM) on the ventilation by means of a human-machine interface (user interface).

The measured values detected by the ventilator and values derived from the measured values, as well as the target values of the ventilation itself, are influenced, changed and partially even distorted, at least from time to time, by the cardiac massage (CM) in such a way that a reliable alarming of the user concerning the quality of the ventilation is not possible during the application of the cardiac massage (CM).

The essential values detected by measurement and measured variables of ventilation derived from measured values include:

Ventilation pressure (P) and its time curve, gradients of the ventilation pressure ($\Delta P/\Delta t$), and volume flow ($\Delta V/\Delta t$).

Derived measured variables and measured values are, for example, respiratory minute volume (MV), minute volume of carbon dioxide ($MVCO_2$), cardiac output (cardiac minute volume).

The following essential target values may be mentioned as examples during ventilation: tidal volume (Vt), respiration rate (RR), mean ventilation pressure. This list of the measured values and measured variables is not comprehensive here, and additional parameters based on physical measured variables for regulating and controlling the ventilation, as well as measured values and measured variables used for the monitoring of ventilation and the patient being ventilated are also covered in the sense of the present invention. These mentioned values are monitored during the controlled mechanical ventilation to determine whether they do not leave a predetermined range (tolerance range) that is safe for the patient, e.g., whether they do not exceed an upper alarm limit, and whether they do not fall below a lower alarm limit, or whether they are located, with a preset variation, around preset values or around a preset curve of the values during a preset time course or time interval. Suitable methods for monitoring the values are threshold value and tolerance monitoring, signal gradient monitoring ($\Delta x/\Delta t$), signal shape and tolerance comparisons, for both individual discrete measured values, time-averaged or filtered measured values or measured value and signal curves. In particular, the pressure measurement is affected very massively by the compression applied to the chest by the cardiac massage (CM). The alarm generation for the user therefore includes an alarm and signal evaluation specially adapted to the method for operating a ventilator which assists cardiopulmonary resuscitation (CPR) or precedes the alarm generation in this embodiment of the method for operating a ventilator which assists cardiopulmonary resuscitation (CPR). The alarm generation for the user takes place typically optically by signaling on a display screen or display, as well as often also additionally acoustically, e.g., by activating a sound-generating element, for example, a horn or a loudspeaker. The alarm and signal evaluation is adapted to the cardiopulmonary resuscitation (CPR) and the cardiac massage (CM) in such a way that specifications or the alarm limits of the measured values affected by the cardiac massage (CM) are raised in case of an upper alarm limit and lowered in case of a lower alarm limit, so that a tolerance range of alarm generation is expanded in its limits upwardly and downwardly, and the original alarm limits set are preferably maintained in a form of intermediate alarm stages.

In a special variant, provisions are made in the method for operating a ventilator which assists cardiopulmonary resuscitation (CPR) for an alarm or at least a signal generation to be delayed in time or to be partially or completely skipped for at least one measured value or at least one measured variable or an event. In another special variant, provisions are made in the method for operating a ventilator which assists cardiopulmonary resuscitation (CPR) for an acoustic alarm to be partially or fully skipped for at least one measured value or at least one measured variable or an event. In another special variant, provisions are made in the method for operating a ventilator which assists cardiopulmonary resuscitation (CPR) for the acoustic alarm to be delayed in time for at least one measured value or at least one measured variable or an event.

The different embodiments and variants of the embodiments of the method for operating a ventilator which assists cardiopulmonary resuscitation (CPR), and of a device designed as a ventilator for mechanical ventilation, which assists cardiopulmonary resuscitation (CPR), which are mentioned in the present application, represent, on the one hand, independent inventive means for accomplishing the object of the present invention, and any possibility of combination of the different embodiments and variants of the embodiments with one another leads to an improvement of the function of the method for operating a ventilator which assists cardiopulmonary resuscitation (CPR) or of the device designed as a ventilator, and they are likewise covered by the embodiments described and shown as well in the sense of the present invention.

One embodiment of a medical system comprises a ventilator with an inspiratory metering unit to assist cardiopulmonary resuscitation (CPR), with an expiratory metering unit, with a control and regulation unit, with an alarm and alarm adaptation unit for monitoring threshold values and tolerance ranges, with a display, signal generation and operating unit for outputting display values, alarms and signals for a user and for inputting setting values by a user, with at least one pressure sensor, with at least one additional sensor, with a sensor and data interface, and with a tube system for the air-carrying connection of the ventilator to a patient. The medical system comprises, furthermore, at least one physiological monitoring device connected to the ventilator via the sensor and data interface of the ventilator for the transmission of data.

The physiological monitoring device is preferably designed as a capnometer or an oximeter/capnometer. The capnometer or oximeter/capnometer is also preferably designed to detect a carbon dioxide concentration ($CO_2$) and/or an oxygen concentration ($O_2$) in the air exhaled by a patient and to transmit it to the ventilator via the sensor and data interface. The alarm and alarm adaptation unit is designed, together with the display and signal generation unit and the control and regulation unit, to change at least one alarm generation on the ventilator. Furthermore, the alarm and alarm adaptation unit is designed, together with the display and signal generation unit, the control and regulation unit and the sensor and data interface, to change at least one alarm generation on the physiological monitoring device. Alarm generation or alarm generation at the ventilator and/or at the at least one physiological monitoring device is defined in the sense of the present invention such that an alarm signal is sent optically or acoustically, optically and acoustically simultaneously or offset in time, and/or that a further or additional external signaling takes place due to the alarm being available in the form of an electric signal at an analog or digital, wired or telemetric data interface. The changes in the alarm generation at the ventilator and/or the change in the alarm generation at the physiological monitoring device preferably cause that those physiological signals that are used by the ventilator to carry out the operation for assisting the cardiopulmonary resuscitation (CPR) are no longer taken into account by the alarm generation at the physiological monitoring device, but those physiological signals that are used by the ventilator to carry out the operation for assisting cardiopulmonary resuscitation (CPR) are taken into account only by the alarm generation of the ventilator. This advantageously leads to the avoidance of multiple alarms in connection with essentially identical causes of alarm and thus relieves the user during the operation and handling of the physiological monitoring device and the ventilator during the operation of the ventilator for assisting cardiopulmonary resuscitation (CPR).

Another embodiment of a medical system comprises a ventilator with an inspiratory metering unit for assisting cardiopulmonary resuscitation (CPR), with an expiratory metering unit, with a control and regulation unit, with an alarm and alarm adaptation unit for monitoring threshold values and tolerance ranges, with a display, signal generation and operating unit for outputting display values, alarms and signals for a user and for inputting setting values by a user, with at least one pressure sensor, with at least one additional sensor, with a sensor and data interface, and with a tube system for the air-carrying connection of the ventilator to a patient.

The further embodiment of the medical system comprises, furthermore, an assist device for the automatic performance of cardiac massage (CM) on the chest of patient. The assist device is designed to perform cardiac massage (CM) on the chest of the patient by means of an element adjustable preferably by means of a motor, electric motor, electromechanically, mechanically, hydraulically or pneumatically, preferably in the form of a chest belt or a holder suitably arranged on the chest. The assist device is connected to the ventilator for data transmission by means of the sensor and data interface. The assist device is able by means of a data transmission to make status information available for the ventilator concerning the current performance of a cardiac massage (CM). The medical system is designed to start or end the operation of the ventilator which assists cardiopulmonary resuscitation (CPR) or to bring the ventilator into a temporary state of pause by means of the status information concerning the current performance of cardiac massage (CM).

Synchronization is made possible in this way between the ventilator, which assists cardiopulmonary resuscitation (CPR), and the assist device. A volume and/or a pressure in the patient's lungs can be adapted to the cardiac massage (CM) such that, on the one hand, the pressure and the volume are higher during a compression by the assist device at the end of the inspiration and before the start of expiration than the pressure and volume that would fill the patient's lungs at the end of the inspiration in case of the application of ventilation with a normal mode of ventilation, i.e., a mode of ventilation without assisted cardiopulmonary resuscitation (CPR). As such the lungs fill part of the chest cavity and thus the heart has reduced possibility to yield in the chest cavity during a compression by the cardiac massage (CM). On the other hand, the pressure and the volume levels during a decompression, by the assist device, at the end of the expiration and before the start of the inspiration by the patient, is such that the lungs are filled essentially only with a volume. The residual volume, that is reduced compared to ventilation with a normal mode of ventilation, without assisted cardiopulmonary resuscitation (CPR), remains in the lungs, so that a backflow of blood from the body to the heart is assisted during a decompression of the chest cavity.

In another preferred manner, the ventilator in the medical system is designed by means of the data transmission to bring the assist device temporarily into a state of pause. This makes it possible for a measurement of pressure and/or flow to be possible at the ventilator without the effect of the assist device, especially in phases with a ventilation situation that is difficult and possible life-threatening for the patient.

Another embodiment of a medical system comprises a ventilator with an inspiratory metering unit for assisting cardiopulmonary resuscitation (CPR), with an expiratory metering unit, with a control and regulation unit, with an alarm and alarm adaptation unit for monitoring threshold values and tolerance ranges, with a display, signal generation and operating unit for outputting display values, alarms and signals to a user, and for inputting setting values by a user, with at least one pressure sensor, with at least one additional sensor, with a sensor and data interface, and with a tube system for the air-carrying connection of the ventilator to a patient.

Furthermore, the medical system comprises a voltage generator for resuscitating the cardiovascular function, preferably a defibrillator. The voltage generator for resuscitating the cardiovascular system or the defibrillator is designed to introduce an electric voltage pulse into the upper body of a patient via at least two electrodes placed on the skin of the chest of a patient and thus to stimulate the cardiovascular function of the patient to resume its independent function. The voltage generator/defibrillator is connected by means of the sensor and data interface of the ventilator for data transmission. The voltage generator/defibrillator is able by means of the data transmission to send a pause signal to the ventilator during the operation of a ventilator which assists cardiopulmonary resuscitation (CPR), especially preferably during phases during which electric voltage pulses are introduced, and to bring the ventilator temporarily into a state of pause. The ventilator stops the ventilation operation in the state of pause during the operation of a ventilator which assists cardiopulmonary resuscitation (CPR) in such a form that inspiratory ventilation strokes are no longer performed, but only the pressure sensor system and preferably additional sensor systems continue to operate, and the ventilator is kept in a standby until the state of pause is ended by the voltage generator/defibrillator via the data transmission. The medical system is designed to bring the ventilator temporarily into a state of pause during the operation of a ventilator which assists cardiopulmonary resuscitation (CPR).

It is preferably made possible in the above-mentioned variants of the medical system by means of the data transmission via the sensor and data interface, preferably by means of control signals exchanged in the medical system, to change an alarm generation on the ventilator and/or on the physiological monitoring device and/or on the voltage generator for resuscitating the cardiovascular function and/or on the assist device for the automatic performance of cardiac massage (CM) in such a way that an alarm, at least a signal generation, is delayed in time and/or partially or completely skipped and/or an acoustic alarm is partially or fully skipped or delayed in time for at least one measured value or for at least one measured variable and/or for at least one event, and/or to vary the volume of at least one alarm for the at least one measured value or for the at least one measured variable or for the at least one event.

The alarm generation is changed in another preferred manner in such a way that alarm limits are raised on the basis of originally set alarm limits in case of an upper alarm limit and/or alarm limits are lowered on the basis of originally set alarm limits in case of a lower alarm limit. This preferably leads to an expansion of a tolerance range for alarming.

Some exemplary embodiments of the present invention are shown in the figures and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 5b is a diagram showing time curves of the ventilation pressure, cardiac massage (CM) and $CO_2$ measurement, chronologically following the time curve of FIG. 5a;

FIG. 5d is a diagram showing time curves of the ventilation pressure, cardiac massage (CM) and $CO_2$ measurement, chronologically following the time curve of FIG. 5c;

DESCRIPTION OF THE PREFERRED EMBODIMENTS

Figure 1A:
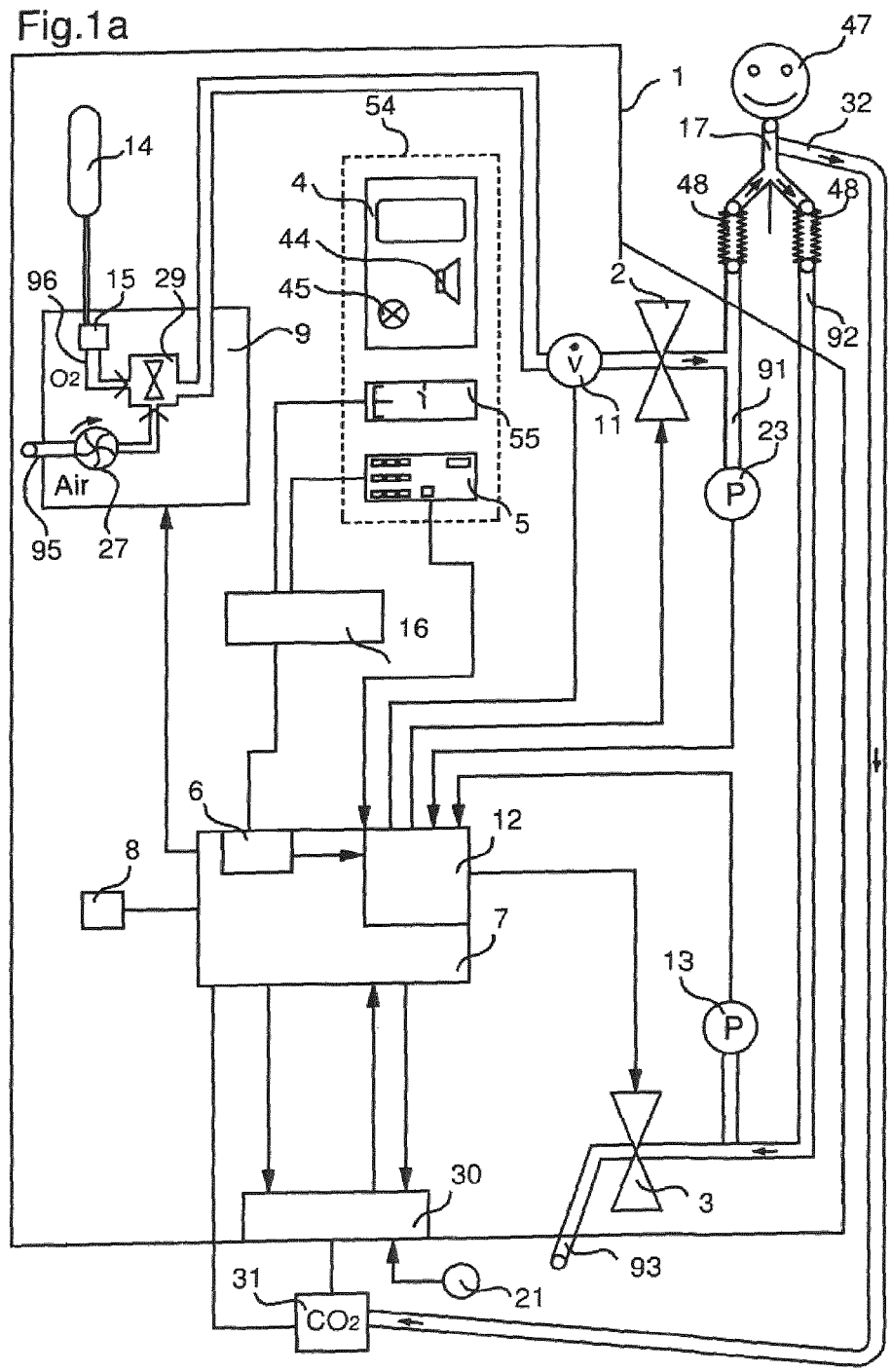
FIG. 1a is a schematic overview of a ventilator.

FIG. 1a shows a first schematic overview of the components of a ventilator 1, which is equipped for performing ventilation. The ventilator 1 has the following components:

An inspiration valve 2, an expiration valve 3, a display and signal generation unit 4, an input unit 5, a control and regulation unit 7, a voltage supply unit 8, a gas-mixing and metering unit 9 with a ventilation drive designed as a blower unit 27 and with an oxygen-air-mixing and metering valve unit 29, and air-gas supply unit 95 and an oxygen gas supply unit 96, a flow-measuring unit 11, a pressure- and flow-regulating unit 12, an expiratory pressure-measuring unit 13, an inspiratory pressure-measuring unit 23, a pressurized oxygen cylinder 14 with a pressure-reducing unit 15, an inspiratory gas port 91, an expiratory gas port 92, and a gas outlet 93. Furthermore, a manipulated variable input 6 is present, by means of which manipulated variables 16 relevant for ventilation, such as respiration rate (RR), pressure amplitude ($P_{amplitude}$), mean positive target pressure (P) of ventilation, tidal volume ($V_T$), I:E ratio ($Ratio_{I:E}$) of the input unit 5, reach the control and regulation unit 7 and are transmitted to the pressure- and flow-regulating unit 12 from there. These manipulated variables 16 are used as preset desired values for the start and for the performance of the ventilation. The patient 47 is connected to the ventilator 1 by means of a connection piece (Y-piece) 17 via an inspiratory gas port 91 and an expiratory gas port 92 by means of two supply lines 48, via a two-tube system in this case shown in FIG. 1a. The exhaled air escapes via the gas port 93 from the ventilator 1 into the surrounding area. An acoustic signal device 44, designed, for example, in the form of a horn or a loudspeaker, as well as an optical signal device 45, designed, for example, as a lamp, an LED or another optical display element, are contained in the display and signal generation unit 4. The input unit 5 may be designed such that it is combined with the display and signal generation unit 4 in a user interface 54, and one or more control elements 55, designed, for example, as key or switching elements or as a keyboard, may also be additionally integrated. The control elements 55 are designed in the present invention to start the method with assisted cardiopulmonary resuscitation (CPR) on the ventilator 1, to control it in interaction with the control and regulation unit 7 and to configure or end it. Furthermore, a data interface 30 is provided on the ventilator 1. Additional sensor systems or accessories may be directly connected via this data interface 30 to the ventilator 1 with a unidirectional or bidirectional data exchange, or a unidirectional or bidirectional exchange of data 21 from the ventilator 1 with external devices may be performed. This FIG. 1a shows as an external physiological sensor a "$CO_2$ sidestream sensor" 31, which draws breathing air from the connection piece (Y-piece) 17 by means of a suction line 32 and analyzes it with respect to the carbon dioxide concentration, and is connected to the data interface 30.

Figure 1B:
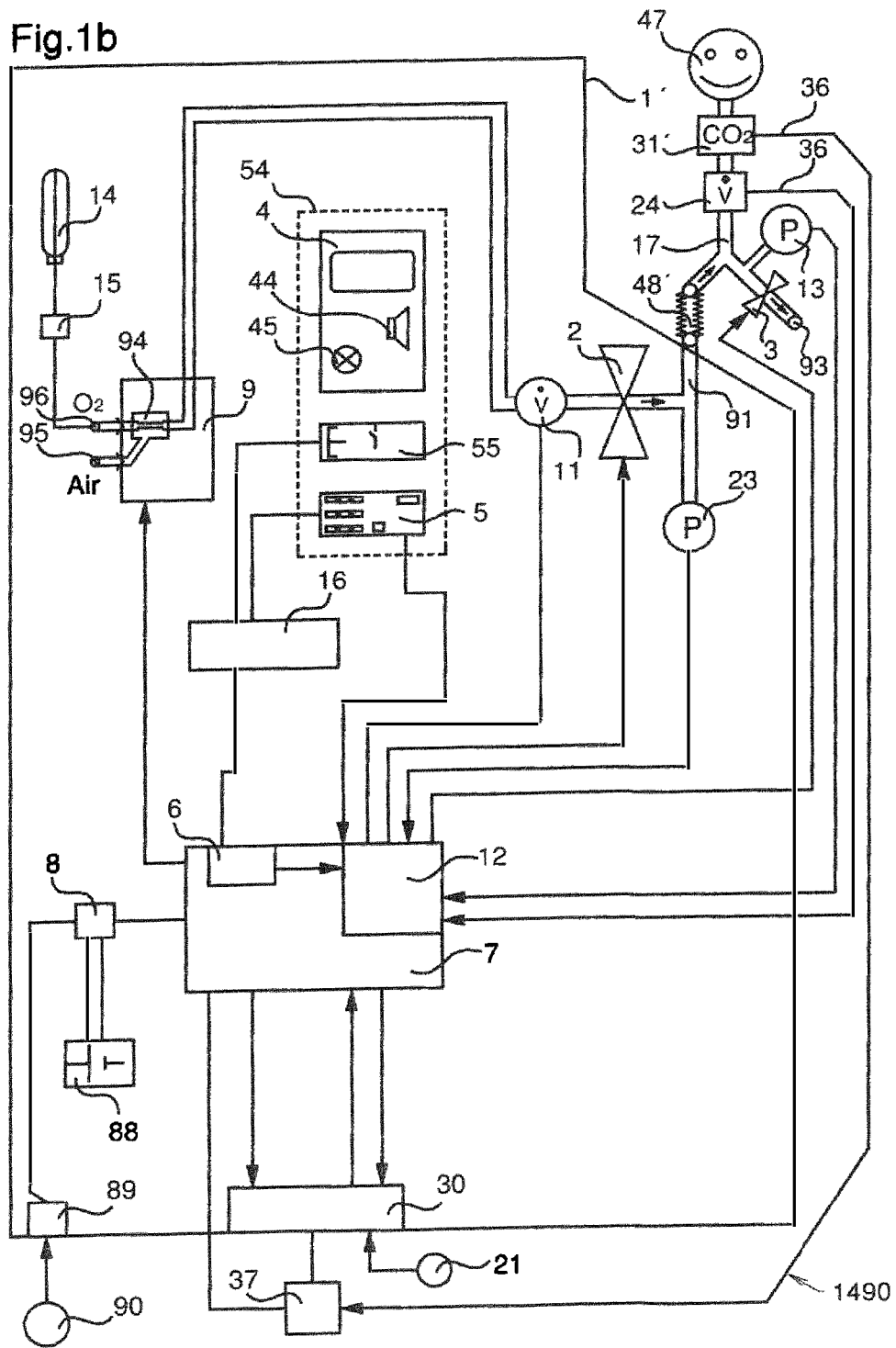
FIG. 1b is a schematic overview of an emergency ventilator.

FIG. 1b shows a second schematic overview of the components of an emergency ventilator 1', which is equipped for performing emergency ventilation. Identical components in FIGS. 1a and 1b are designated by the same reference numbers. The emergency ventilator 1' has the following components:

An inspiration valve 2, an expiration valve 3, a display and signal generation unit 4, an input unit 5, a control and regulation unit 7, a voltage supply unit 8, a gas-mixing and metering unit 9 with an ejector 94, an air-gas supply unit 95 and an oxygen gas supply unit 96, a flow-measuring unit 11, a pressure- and flow-regulating unit 12, an expiratory pressure-measuring unit 13', an inspiratory pressure-measuring unit 23, a pressurized oxygen cylinder 14 with a pressure-reducing unit 15, and an inspiratory gas port 91. Furthermore, a manipulated variable input 6 is present, by means of which manipulated variables 16 relevant for ventilation, such as respiration rate (RR), pressure amplitude ($P_{amplitude}$), mean positive target pressure (P) of the ventilation, tidal volume ($V_T$), I:E ratio ($Ratio_{I:E}$), reach the control and regulation unit 7 from the input unit 5 and are transmitted from there to the pressure- and flow-regulating unit 12. These manipulated variables 16 are used as desired specifications for the start and for the performance of the emergency ventilation. The patient 47 is connected to the emergency ventilator 1 by means of a connection piece (Y-piece) 17 via an inspiratory gas port 91 by means of a supply line 48', in this case shown in this FIG. 1b via a one-tube system. The exhaled air escapes via a gas outlet 93' directly at the connection piece 17 into the surrounding area. An acoustic signal device 44, designed, for example, in the form of a horn or a loudspeaker, as well as an optical signal device 45, designed for example, as a lamp, an LED or another optical display element, are contained in the display and signal generation unit 4. The input unit 5 may be designed such that it is combined with the display and signal generation unit 4 in a user interface 54, and one or more control elements 55, designed, for example, as keys or switching elements or as a keyboard, may also be additionally integrated. The control elements 55 are designed in the present invention to start the method with assisted cardiopulmonary resuscitation (CPR) on the emergency ventilator 1', to control the CPR in interaction with the control and regulation unit 7 and to configure or end it. Furthermore, an interface is provided for electric energy 90. A rechargeable battery pack 88, which can be supplied with electric energy and charged from the outside by means of an energy-charging and supply element 89 and via the interface for electric energy 90, is connected to the voltage supply unit 8. Furthermore, a data interface 30 is provided on the emergency ventilator 1'. Additional sensors or additional devices may be connected directly via this data interface 30 to the emergency ventilator 1' with a unidirectional or bidirectional data exchange, or data 21 of external devices can be exchanged unidirectionally or bidirectionally with the emergency ventilator 1' via the data interface 30.

A physiological sensor 31' designed as a "$CO_2$ mainstream sensor" for determining a carbon dioxide concentration ($CO_2$) in the breathing gas of the patient 47 and a flow sensor 24 located close to the patient for determining the flow rates to and from the patient 43 at the connection piece (Y-piece) 17 are connected as additional sensors to the emergency ventilator 1' in this FIG. 1b. The physiological sensor 31' and the flow sensor 24 located close to the patient transmit measured values to a corresponding $CO_2$ analyzer 37 by means of data lines 36. The corresponding analyzer 37 further transmits the measured values via the data interface 30 to the emergency ventilator 1'. The arrangement of the "$CO_2$ mainstream sensor" 31' and of the flow sensor 24 located close to the patient at the connection piece in the proximity of each other in space is especially advantageous for forming a variable derived from the measured values of these two sensors, a "minute volume of carbon dioxide," $MVCO_2$. This minute volume $CO_2$ ($MVCO_2$) can advantageously be used to assess the quality of a cardiac massage (CM) being performed in the device for assisting cardiopulmonary resuscitation (CPR) as well as in the method for assisting cardiopulmonary resuscitation (CPR). As is shown in more detail in FIGS. 7a and 7b, additional external devices, for example, a voltage generator for resuscitating the cardiovascular function (defibrillator) or an assist device for automatically performing a cardiac massage (CM) can be connected to the ventilator 1 (FIG. 1a) via the data interface 30, so that, on the one hand, information and/or data from the external device, for example, ECG signals of the defibrillator, and, on the other hand, also information from the ventilator 1, 1' to the external device for controlling the latter, for example, start/stop/pause signals, can be exchanged in order to assist the device for assisting cardiopulmonary resuscitation (CPR) and to also include it in the method for assisting cardiopulmonary resuscitation (CPR).

FIG. 1b schematically shows a variant of a medical system 1490 with the ventilator 1' combined with the $CO_2$ analyzer 37 connected via the sensor and data interface 30 and with the carbon dioxide sensor 31' connected by means of data line 36 as a physiological sensor.

Another, and essentially similar medical system is obtained according to FIG. 1a with the ventilator 1 combined with the physiological sensor 31 connected via the sensor and data interface 30.

Figure 2:
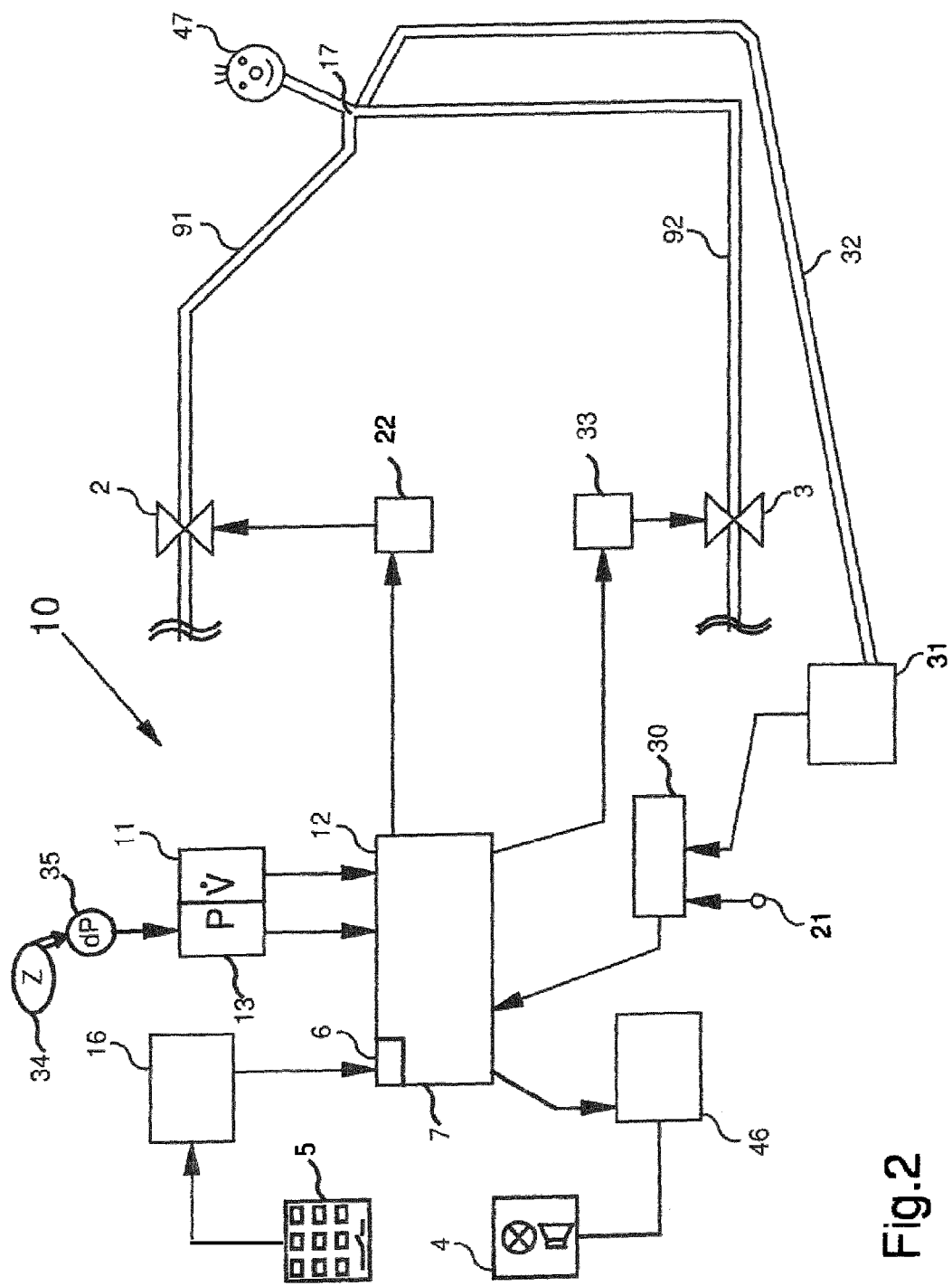
FIG. 2 is a schematic diagram of a ventilation control according to FIGS. 1a and 1b.

In a diagram 10, FIG. 2 shows essential elements of the ventilator 1, 1" according to FIGS. 1a, 1b for the performance of the method for operating a ventilator which assists cardiopulmonary resuscitation (CPR). Identical elements in FIGS. 1a, 1b are designated by the same reference numbers as in FIG. 2. Corresponding to FIGS. 1a, 1b, the inspiration valve 1, the expiration valve 3, the display and signal generation unit 4, the input unit 5, the pressure-measuring unit 13, the flow-measuring unit 11, the control and regulation unit 7 with the pressure- and flow-regulating unit 12 and with the manipulated variable input 6 for the input variables 16, the data interface 30 for data 21, and the device 31 designed as a $CO_2$ sensor, which is in air-carrying connection with the patient 47 via the suction line 32 and the connection piece 17, are shown. The patient is connected to the ventilator 1, 1' (FIGS. 1a, 1b) via the inspiratory gas port 91 and the expiratory gas port 93 and the connection piece. The following elements are shown in detail for illustration in this diagram 10 in FIG. 2. An adaptation and time lag element 22 is symbolically arranged upstream of the inspiration valve 2 in this diagram 10 in FIG. 2. An adaptation and time lag element 33 is likewise symbolically arranged upstream of the expiration valve 3 in this diagram 10. The adaptation and time lag elements 22, 33 are preferably embodied technically as components of the control and regulation unit 7. The inspiratory time lag element 22 and the expiratory time lag element 33 are actuated by the control and regulation unit 7 and activated during the operation of the ventilator 1, 1' (FIGS. 1a, 1b) with assisted cardiopulmonary resuscitation (CPR) in such a way that the regulation of the ventilation does not respond directly to any changes in the measured ventilation pressure. Furthermore, the expiratory time lag element 33 is actuated by the control and regulation unit 7 such that the start of the expiration phase is delayed during the operation of the ventilator with assisted cardiopulmonary resuscitation (CPR). Furthermore, the inspiratory time lag element 22 is actuated by the control and regulation unit 7 such that the start of the inspiration phase is delayed during the operation of the ventilator with assisted cardiopulmonary resuscitation (CPR). Furthermore, this diagram 10 shows that an alarm and alarm adaptation unit 46 is inserted between the control and regulation unit 7 and the display and signal generation unit 4.

The alarm and alarm adaptation unit 46 is preferably designed in one technical implementation as a part of the control and regulation unit 7 or of the display and signal generation unit 4 or as part of the operating system of the ventilator 1 (FIG. 1a, 1b). A symbolic interference variable Z 34 is shown, which represents the effect of the cardiac massage (CM) in the form of pressure changes dP 35 on the pressure measurement 13 as well as indirectly also on the flow measurement 11. The pressure variation effect on the signal of the ventilation pressure P 610 (FIGS. 5a through 5e), which is caused by the cardiac massage (CM), becomes clear especially in the diagrams according to FIG. 5c. The adaptation and time lag elements 22, 33 are used in the method for operating a ventilator for assisting cardiopulmonary resuscitation (CPR) to delay the start of the inspiration phase and the start of the expiration phase in order to assist the cardiac massage (CM). The assist takes place in the expiration phase by the delay caused by the expiratory time lag element 33 bringing about an increase in the initial expiratory pressure level and hence an increase in an air-filled volume of the patient's lungs, so that the lungs will fill a part of the chest cavity and the heart will thus have a reduced possibility to yield in the chest cavity during a compression by the cardiac massage (CM). The assist takes place during the inspiration phase by the delay caused by the inspiratory time lag element 22 leading to a reduction of an initial inspiratory pressure level in the patient's lungs and generating a slight vacuum in the lungs in relation to the ambient pressure by a supply of fresh breathing air at the start of the inspiration phase being delayed in time by a delay with which the inspiration valve 2 opens. The pressure in the chest cavity is thus reduced during the performance of the method for operating a ventilator for assisting cardiopulmonary resuscitation (CPR), so that the backflow of the blood from the body to the heart during the decompression of the chest cavity is assisted. The alarm and alarm adaptation unit 46 is used in the method for operating a ventilator for assisting cardiopulmonary resuscitation (CPR), so that alarms that would be triggered by the cardiac massage (CM) due to the interference variable Z 34, e.g., as pressure changes dP 35, which is superimposed to the signal of the ventilation pressure, which latter signal is caused by the ventilation, are treated such that the alarm generation to the user is partially, temporarily or fully suppressed for the duration during which the method for operating a ventilator with assisted cardiopulmonary resuscitation (CPR) is being carried out. The interference variable may also be filtered in respect to its amplitude or duration.

Figure 3:
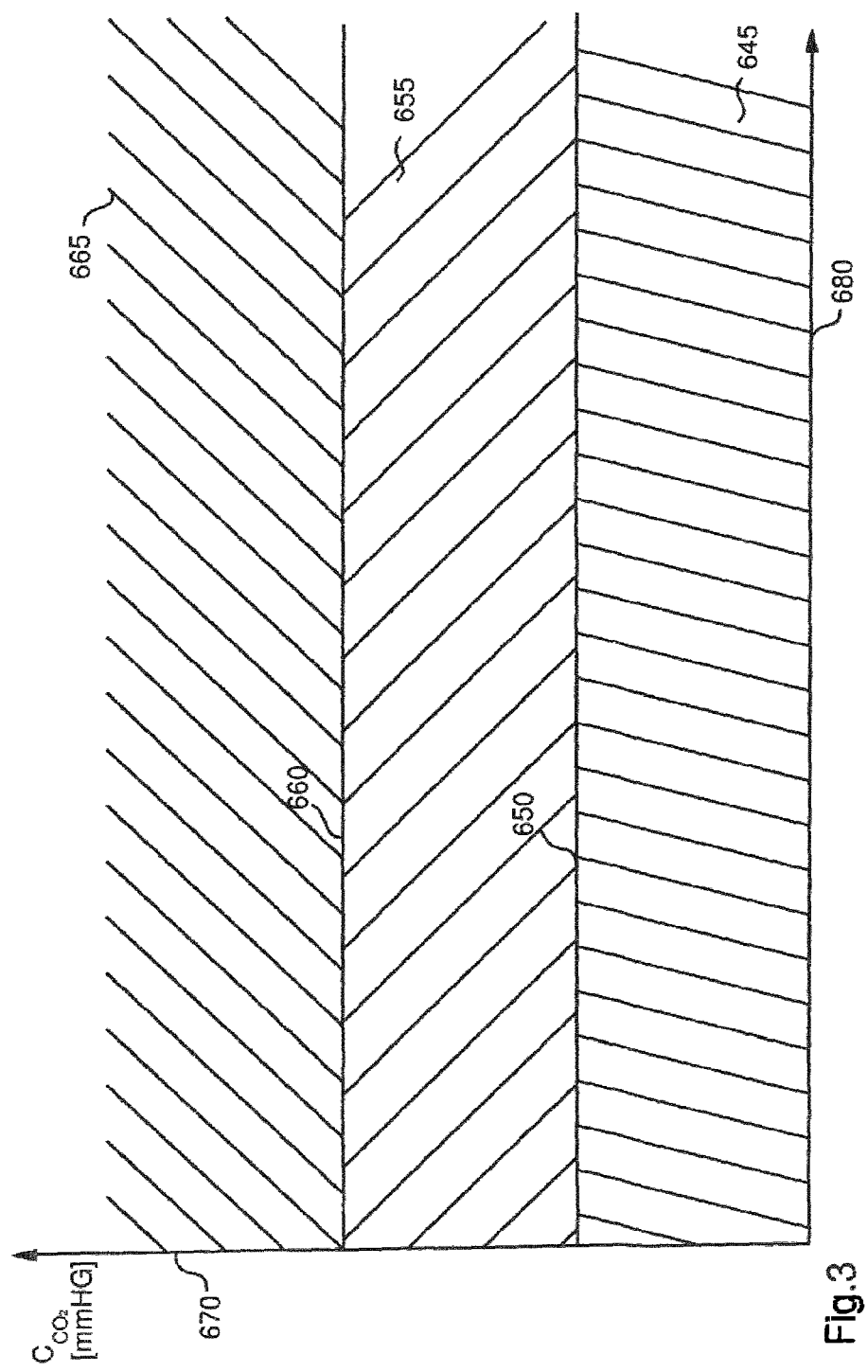
FIG. 3 is a diagram of concentration ranges of the $CO_2$ concentration.

FIG. 3 shows how a predetermined first threshold value 650 and a predetermined second threshold value 660 of the $CO_2$ concentration divide the diagram of a $CO_2$ concentration 506 into three concentration ranges 645, 655, 665. The $CO_2$ concentration is shown in the unit mmHg on the ordinate 670, and the time course is plotted in a dimensionless form on the abscissa 680.

A first concentration 645 is obtained, in which the $CO_2$ concentration is below the first predetermined threshold value 650. The fact that this first predetermined threshold value 650 is not reached indicates that the cardiac massage (CM) is not being performed in a sufficient manner to maintain the patient's cardiovascular function. There is a second concentration range 655, in which the $CO_2$ concentration is above the first predetermined threshold value 650 and below the second predetermined threshold value 660. The fact that the second predetermined threshold value 660 is not reached indicates that the patient is not able to maintain his cardiovascular function on his own and cardiac massage (CM) should therefore be applied by the user. There is a third concentration range 665, in which the $CO_2$ concentration is above the second predetermined threshold value 660. The fact that the second predetermined threshold value is exceeded indicates that the patient is able on his own to maintain his cardiovascular function and no cardiac massage (CM) is therefore necessary, as well as that a cardiac massage (CM) currently being applied by the user should be ended. A first predetermined threshold value 650 of 10 mmHg with a variation of +/−2 mmHg and a second predetermined threshold value 660 of 40 mmHg with a variation of +/−2 mmHg are suitable values for the practical use of the ventilator 1, 1' (FIG. 1a, FIG. 1b) with assisted cardiopulmonary resuscitation (CPR) in emergency medicine. When the first predetermined threshold value 650 and the second predetermined threshold value 660 are not reached and exceeded, further and additional criteria may be used and linked with one another for triggering the messages (FIG. 4) for the user for starting the operation of ventilation with assisted cardiopulmonary resuscitation (CPR) and for regulating (FIG. 2) the ventilation pressure (FIG. 2) during the operation of the ventilator with assisted cardiopulmonary resuscitation (CPR).

Such further and additional criteria are, for example, measured values and/or setting parameters of the ventilator or measured values and/or setting parameters of a physiological monitor. An oxygen concentration is mentioned as an example of setting parameters of a ventilator.

An oxygen partial pressure $SPO_2$ in the blood or a non-invasively detected blood pressure (NBP) or a heart rate (HR) of the patient are mentioned as examples of measured values of a physiological monitor, besides the $CO_2$ concentration.

Figure 4:
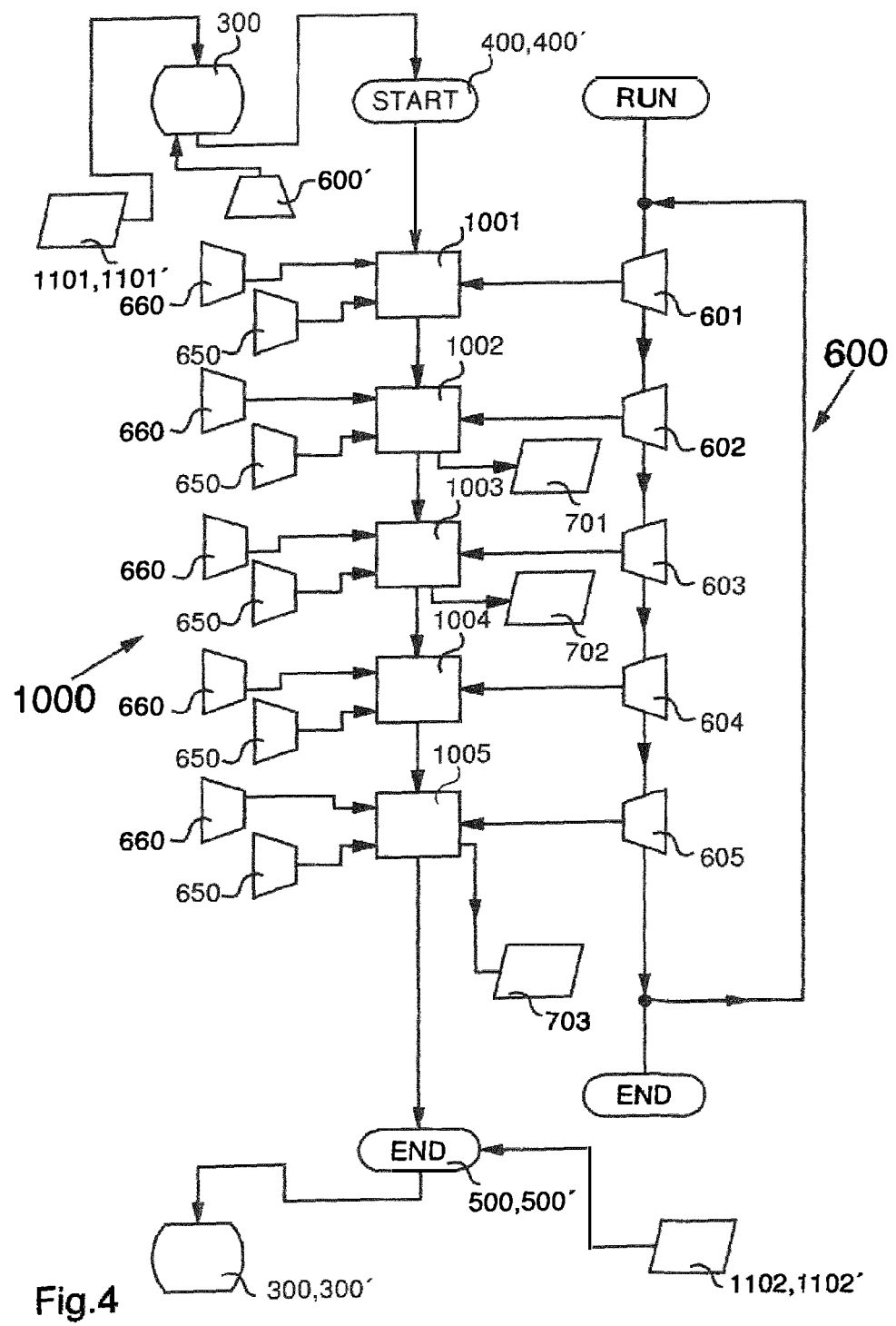
FIG. 4 is a schematic sequence of the method for operating a ventilator which assists cardiopulmonary resuscitation (CPR)

FIG. 4 shows a schematic sequence 1000 with the start and end of the method for operating a ventilator for assisting cardiopulmonary resuscitation (CPR). The sequence 1000 is divided into a time course of the ventilation of a patient 47 (FIGS. 1a, 1b, 2) with any desired, originally selected ventilation mode 300, in which no cardiac massage (CM) is being performed on the patient 47 (FIG. 1, 2).

A start 400 of the method for operating the ventilator 1, 1' (FIGS. 1a, 1b) with assisted cardiopulmonary resuscitation (CPR) is triggered by a first user interaction 1101 from any desired ventilation mode 300. The ventilation of any desired mode 300 may be a pressure- or volume-controlled ventilation mode. A physiological sensor or an external monitoring device 31, 31' (FIGS. 1a, 1b) provides in the desired ventilation mode 300 current measured signals 600' of a current carbon dioxide concentration, as well as measured signals 601, 602, 603, 604, 605 of a current carbon dioxide concentration are provided in the method for operating the ventilator 1, 1' (FIGS. 1a, 1b) with assisted cardiopulmonary resuscitation (CPR) in a continuously repeating sequence 600 at predetermined time intervals as input variables for the sequence 1000 of the method for operating the ventilator 1 (FIG. 1a, 1b) with assisted cardiopulmonary resuscitation (CPR). The start 400 of the method for operating the ventilator 1, 1' (FIGS. 1a, 1b) with assisted cardiopulmonary resuscitation (CPR) may take place by the first user interaction 1101 or else even automatically by the ventilator 1, 1' (FIGS. 1a, 1b), e.g., on the basis of the measured signals 600' of the current carbon dioxide concentration, without a user interaction. As an alternative, a start 400' may also take place semi-automatically by the ventilator 1, 1' (FIGS. 1a, 1b), e.g., on the basis of the measured signals 600' of the current carbon dioxide concentration, the start 400' being suggested by the ventilator 1 (FIG. 1a, 1b) via the combined display, signal generation and input unit 54 (FIGS. 1a, 1b), and the start 400' is then finally acknowledged by a first user interaction 1101', and the ventilator 1, 1' (FIGS. 1a, 1b) will then change over to the operation of the ventilator 1, 1' (FIGS. 1a, 1b) with assisted cardiopulmonary resuscitation (CPR) 1000. The measured signals 601, 602, 603, 604, 605 of the current carbon dioxide concentration, which are detected continuously in the sequence 600, are evaluated in the sequence 1000. The relation of the carbon dioxide concentration to the first predetermined threshold value 650 and the relation of the carbon dioxide concentration to the second predetermined threshold value 660 are checked by a comparison in this analysis in the sequence 1000. As an example, the sequence 1000 is divided in this FIG. 4 into phases 1001, 1002, 1003, 1004, 1005, in which the current carbon dioxide concentration is compared with the first predetermined threshold value 650 and with the second predetermined threshold value 660. The timing of the phases 1001, 1002, 1003, 1004, 1005 in the sequence may follow each other, as is shown in FIG. 4, but the present invention also covers the case in which the phases 1001, 1002, 1003, 1004, 1005 may occur without a chronological coordination or coordinated with one another at any desired time during the ventilation or in the course of the ventilation during the treatment or emergency treatment of a patient. The duration in time of the individual phases 1001, 1002, 1003, 1004, 1005 depends in this case on the treatment situation, the patient's constitution and the assessment made by the user in this regard. Furthermore, the duration in time of the individual phases 1001, 1002, 1003, 1004, 1005 indirectly depends on the selection of the first predetermined threshold value 650 and of the second predetermined threshold value 660, as well as on the relation of the threshold values 650, 660 to one another. In the first phase 1001 of the sequence 1000, the comparison shows that the current carbon dioxide concentration 601 is above the first predetermined threshold value 650 and below the second predetermined threshold value 660 and is thus in a second concentration range of the $CO_2$ concentration 655 (FIG. 3). This is evaluated as an indication that the cardiovascular situation is being carried out successfully for supplying the organs with oxygen by means of the cardiac massage (CM). In the second phase 1002 of the sequence 1000, the comparison shows that the current carbon dioxide concentration 602 is below the first predetermined threshold value 650 and below the second predetermined threshold value 660 and it is thus in a first concentration range of the $CO_2$ concentration 645 (FIG. 3). This is evaluated as an indicator that the cardiac massage (CM) is not being performed in a sufficient manner to replace the patient's cardiovascular function and to supply the vital organs, especially the brain, with a sufficient amount of oxygen. A first message 701 is sent to the user that the cardiac massage (CM) is not being performed properly. In the third phase 1003 of the sequence 1000, the comparison shows that the current carbon dioxide concentration 603 is again above the first predetermined threshold value 650 and below the second predetermined threshold value 660 and is consequently in a second concentration range of the $CO_2$ concentration 655 (FIG. 3). This is evaluated as an indication that the cardiovascular function is again being performed successfully for supplying the organs with oxygen by means of the cardiac massage (CM). A second message 702 is sent to the user that the cardiac massage (CM) is again being performed properly. The comparison shows, in the fourth phase 1004 of the sequence 1000, that the current carbon dioxide concentration 604 continues to be above the first predetermined threshold value 650 and below the second predetermined threshold value 660. The comparison shows in the fifth phase 1005 of the sequence 1000 that the current carbon dioxide concentration 605 is above the first predetermined threshold value 650 and above the second predetermined threshold value 660 and is thus in a third concentration range of the $CO_2$ concentration 665 (FIG. 3). This is evaluated as an indication that the cardiovascular function with the supply of the organs with oxygen is again maintained by the patient independently. A third message 703 is sent to the user that the cardiovascular function of the patient can again be maintained independently. The fifth phase 1005 of the sequence thus passes over, for example, in this FIG. 4, to the ending 500 of the method for operating the ventilator 1, 1' (FIGS. 1a, 1b) with assisted cardiopulmonary resuscitation (CPR). An ending 500 of the method for operating the ventilator 1, 1' (FIGS. 1a, 1b) with assisted cardiopulmonary resuscitation (CPR) is triggered by a second user interaction 1102 in this FIG. 4. The ventilation of the patient 47 (FIGS. 1, 2) is then continued with any desired, originally selected ventilation mode 300 or with any other desired ventilation mode 300'. The any desired ventilation mode 300, 300' may be a pressure- or volume-controlled ventilation mode. However, the ending 500 may also be brought about automatically by the ventilator 1 (FIGS. 1a, 1b) without a user interaction, or an ending 500' may also be brought about semi-automatically by the ventilator 1, 1' (FIGS. 1a, 1b), in which case the ending 500 is suggested by the ventilator 1, 1' (FIGS. 1a, 1b) via the combined display, signal generation and input unit 54 (FIGS. 1a, 1b), and the ending 500' is finally acknowledged by a user interaction 1102', and the ventilator 1, 1' (FIGS. 1a, 1b) will then switch over to the any desired ventilation mode 300, 300'.

FIGS. 5a through 5e show exemplary diagrams 501, 502, 503, 504, 505 of the time courses of a mechanical ventilation of a patient with a cardiac massage (CM) being performed simultaneously.

FIGS. 5a through 5e have an abscissa 640 and three ordinates 630, which coordinate system shows, synchronously in time and horizontally one above another, the time courses of a ventilation pressure P 610 of the patient. These are diagrams illustrating whether a cardiac massage (CM) is being applied, which is designated as a so-called CM activity 615 in the present invention, as well as a $CO_2$ concentration $cCO_2$ 620.

The ventilation pressure P 610 of the patient is usually measured and scaled, in medical practice, in the dimensions $mmH_2O$ or mbar or hPa. The CM activity 615 is dimensionless. The $CO_2$ concentration $cCO_2$ 620 is usually measured and scaled, in medical practice, in the dimension mmHg. These are shown for different phases of a typical emergency ventilation situation.

The curves 610, 620 and their chronological assignment to one another correspond in FIGS. 5a through 5e, in principle, to a conversion with a "$CO_2$ sidestream sensor" 31 (FIG. 1a). The chronological assignment is shown only as an example in FIGS. 5a through 5e, because a plurality of marginal conditions, for example, the length of the supply lines 48, 48' (FIGS. 1a, 1b), the length and diameter of the suction line 32 (FIG. 1a), the time characteristic of the components involved and of the signal processing, play an essential role in practice. A fundamentally different chronological assignment, which would be improved in terms of the chronological synchronicity of the curves 610, 620, because different marginal conditions would now become noticeable, would be obtained when using a "$CO_2$ mainstream sensor" 31 (FIG. 1b).

Figure 5A:
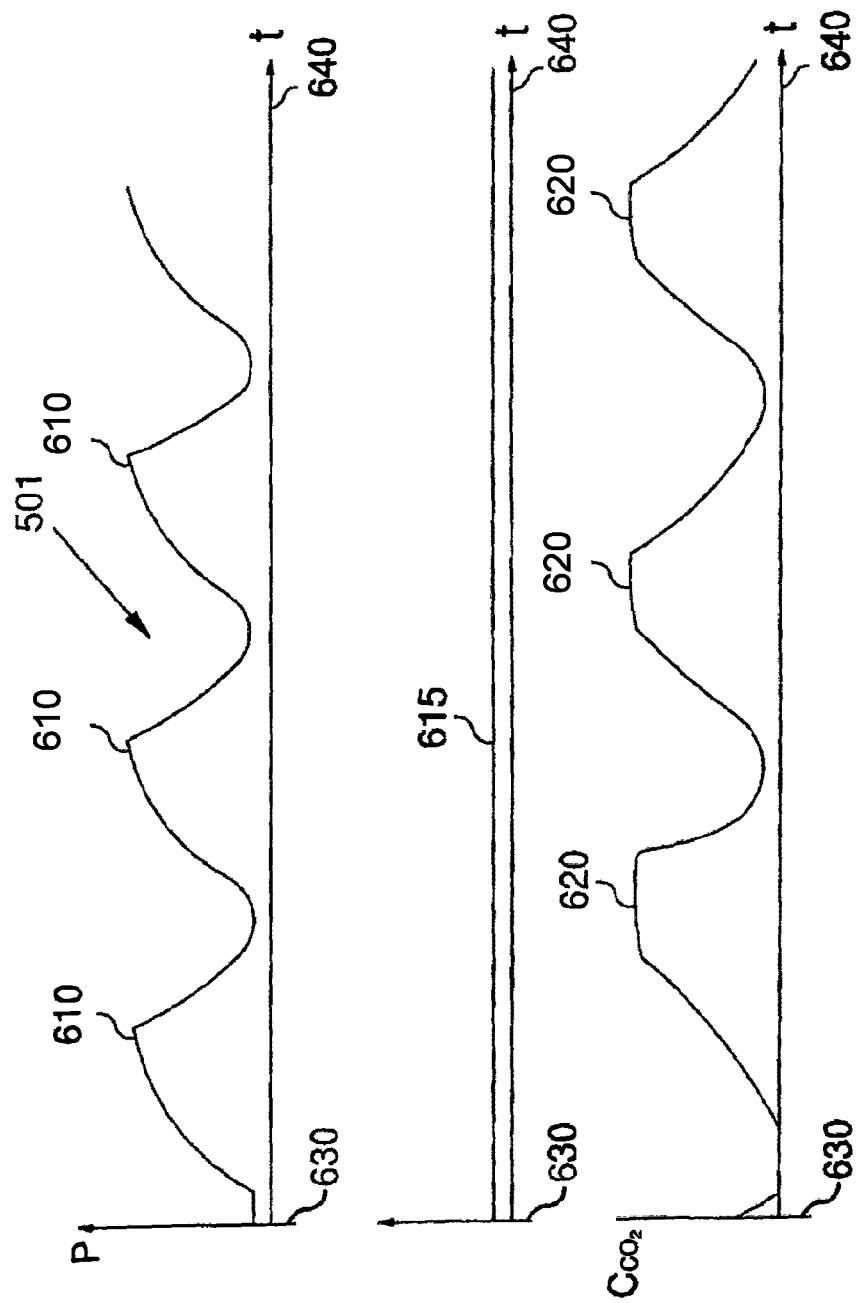
FIG. 5a is a diagram showing time graphs of the ventilation pressure, cardiac massage (CM) and $CO_2$ measurement.

FIGS. 5a through 5a are explained in more detail with a joint description of the Figures. A typical sequence of events in an emergency situation of a patient being ventilated, with the need for and the application of a temporary cardiac massage (CM) or cardiopulmonary resuscitation, is shown in a simplified manner and schematically in the signal curves 501, 502, 503, 50-4, 505 of the ventilation pressure 610 and of the carbon dioxide concentration 620 along with the effect of the cardiac massage (CM) 615 on the signal curves of the ventilation pressure 610 and of the carbon dioxide concentration 620.

Mechanical ventilation is assumed in the diagram 501 according to FIG. 5a, with the patient intubated or connected to the ventilator 1, 1' (FIGS. 1a, 1b) via a mask and being ventilated, with a physiological monitoring being connected to detect the patient's vital parameters, the $CO_2$ concentration 620 being measured as the at least one vital parameter. Measured values of the physiological monitoring, including also the current value of the $CO_2$ concentration 620, are available to the ventilator 1, 1' (FIGS. 1a and 1b) via a data interface 30 (FIGS. 1a, 1b). The value of the $CO_2$ concentration 620 is, on average, above a first predetermined threshold value 650 in the third concentration range of the $CO_2$ concentration 665 (FIG. 3), which indicates that the cardiovascular function of the patient is spontaneous and stable. It is not necessary to apply cardiac massage (CM) 615, and the ventilator 1, 1' operates in a first mode of operation.

In these exemplary diagrams of the time curves 501, 502, 503, 504, 505 of a mechanical ventilation of a patient with cardiac massage (CM) being performed simultaneously, FIG. 5b showing the time curve 502 follows chronologically the curve 501 of the mechanical ventilation of a patient without simultaneously performed cardiac massage (CM) according to FIG. 5a.

In diagram 502 according to FIG. 5b, the $CO_2$ concentration 620 of the patient drops at a time T1 in the course of the ventilation below the first predetermined threshold value 650 into the first concentration range of the $CO_2$ concentration 645 (FIG. 3). Triggered by the fact that the first predetermined threshold value 650 is not reached, the ventilator 1, 1' (FIGS. 1a, 1b) sends an alarm (FIG. 4) to the user, indicating that the cardiovascular function of the patient is currently not given. In addition, a message (FIG. 4) is sent to the user in the further time course, indicating that the ventilator has made preparations for a changeover into the operation of a ventilator with assisted cardiopulmonary resuscitation (CPR), i.e., into the second mode of operation, and is awaiting a final acknowledgement by the user to activate the operation of the ventilator with assisted cardiopulmonary resuscitation (CPR) or will automatically perform the changeover into the operation of the ventilator with assisted cardiopulmonary resuscitation (CPR). An automatic changeover into the operation of the ventilator with assisted cardiopulmonary resuscitation (CPR), i.e., into the second mode of operation, may be triggered now, for example, by the circumstance that the first predetermined threshold value 650 of the carbon dioxide concentration is not reached for a longer time than a predetermined first duration. The ventilator (FIG. 1a, 1b) will then change over into the operation of the ventilator with assisted cardiopulmonary resuscitation (CPR) (second mode of operation) automatically or by an activation initiated by the user, and sends a corresponding message (FIG. 4). The user starts the cardiac massage (CM), and the time curve of the ventilation pressure shows, chronologically after the first time T1 621, the effect of the cardiac massage (CM) in the form of a superimposition of pressure peaks with the frequency of the cardiac massage (CM).

Figure 5C:
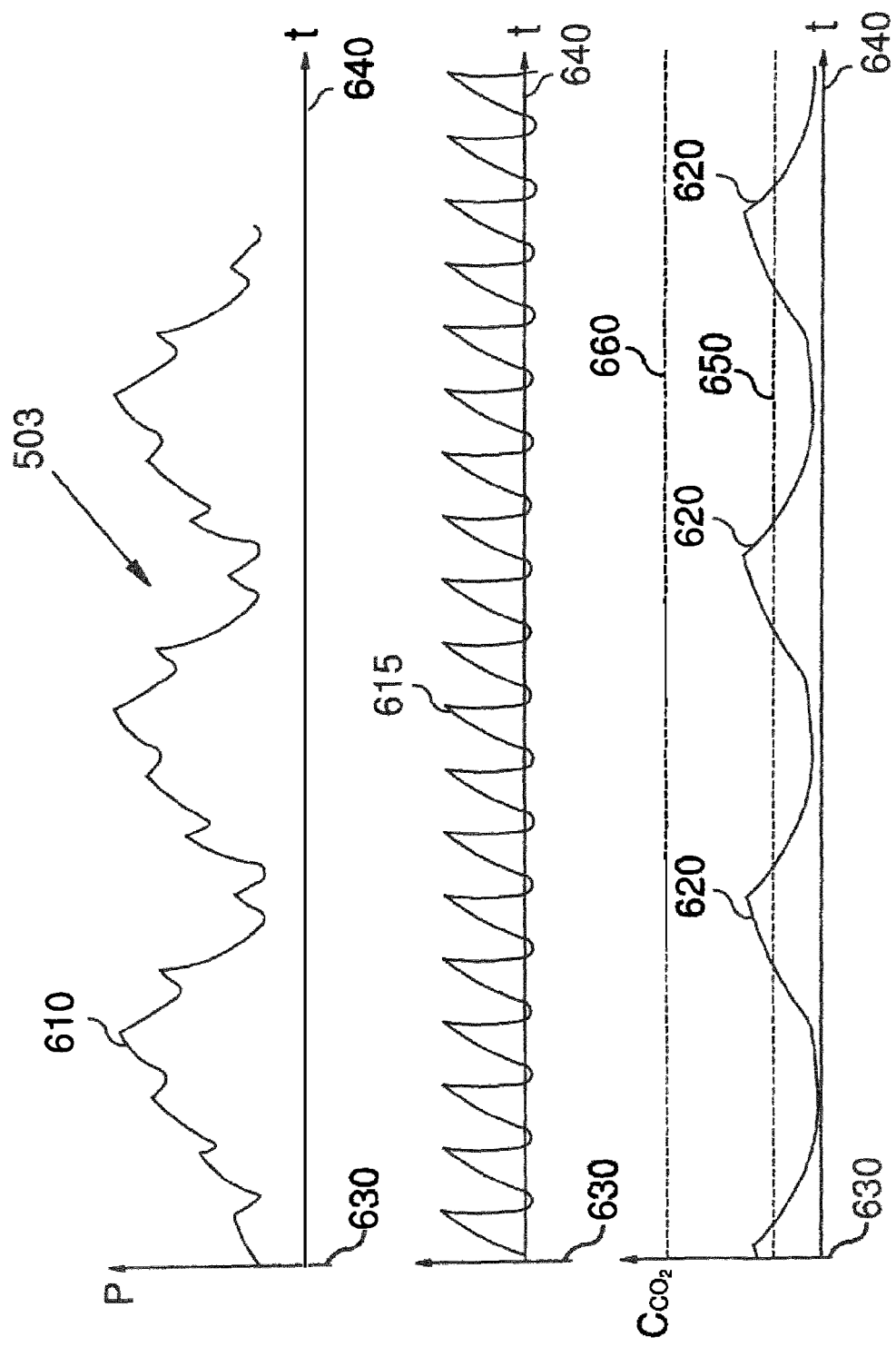
FIG. 5c is a diagram showing time curves of the ventilation pressure, cardiac massage (CM) and $CO_2$ measurement, chronologically following the time curve of FIG. 5b.

In these exemplary diagrams of the time curves 501, 502, 503, 504, 505 of the mechanical ventilation of a patient with simultaneously performed cardiac massage (CM) (second mode of operation), FIG. 5c shows the time curve 503 follows chronologically the curve 502 of the mechanical ventilation of a patient with simultaneously performed cardiac massage (CM) according to FIG. 5b.

In diagram 503 according to FIG. 5c, the cardiac massage (CM) started in FIG. 5b persists while the mechanical ventilation is maintained. However, the patient's $CO_2$ concentration rises to above the first predetermined threshold value 650 in the course of the cardiac massage (CM) due to the cardiac massage (CM). However, the patient's $CO_2$ concentration continues to be below the second predetermined threshold value 660 in the second concentration range of the $CO_2$ concentration 655 (FIG. 3), which indicates that the ventilation and the cardiac massage (CM) are being performed in such a way that both the pulmonary ventilation is maintained due to the ventilation and the cardiovascular function is maintained for supplying the organs with oxygen by means of the cardiac massage (CM), but the patient is still unable to independently assume and maintain the cardiocirculatory function. The time curve of the ventilation pressure 610 shows the effect of the cardiac massage (CM) in the form of a superimposition of pressure peaks with the frequency of the cardiac massage (CM).

In these exemplary diagrams of the time curves 501, 502, 503, 504, 505 of the mechanical ventilation of a patient with simultaneously performed cardiac massage (CM), FIG. 5d shows the time curve 504 follows chronologically the curve 503 of the mechanical ventilation of a patient with simultaneously performed cardiac massage (CM) according to FIG. 5c.

The diagram 504 according to FIG. 5d shows the time curve of a ventilation with simultaneous cardiac massage (CM), during which the $CO_2$ concentration 620 of the patient is at times below the first predetermined threshold value 650 in the first concentration range of the $CO_2$ concentration 645 (FIG. 3). When the first predetermined threshold value 650 is not reached at a second time T2 622, the ventilator 1, 1' (FIGS. 1a, 1b) sends a message (FIG. 4) to the user in the method of operation of a ventilator 1, 1' (FIGS. 1a, 1b), indicating that the cardiac massage (CM) is not being performed in a sufficient manner to replace the patient's cardiovascular function and to supply the vital organs, especially the brain, with a sufficient quantity of oxygen. This happens, for example, when the pressure massage (CM) is not being performed with a sufficient pressure or the time intervals between the individual administrations of the pressure massage (CM) on the chest of the patient are too long or the cardiac massage (CM) as a whole is being performed irregularly. The time curve of the ventilation pressure 610 also shows at the second time T2 622 that the cardiac massage (CM) 615 is not being performed properly, because the superimposition of pressure peaks with the frequency of the cardiac massage (CM) is no longer visible. Cardiac massage (CM) 615 is performed again, as a whole, properly in the further course of this diagram, following chronologically the second time T2 622.

Figure 5E:
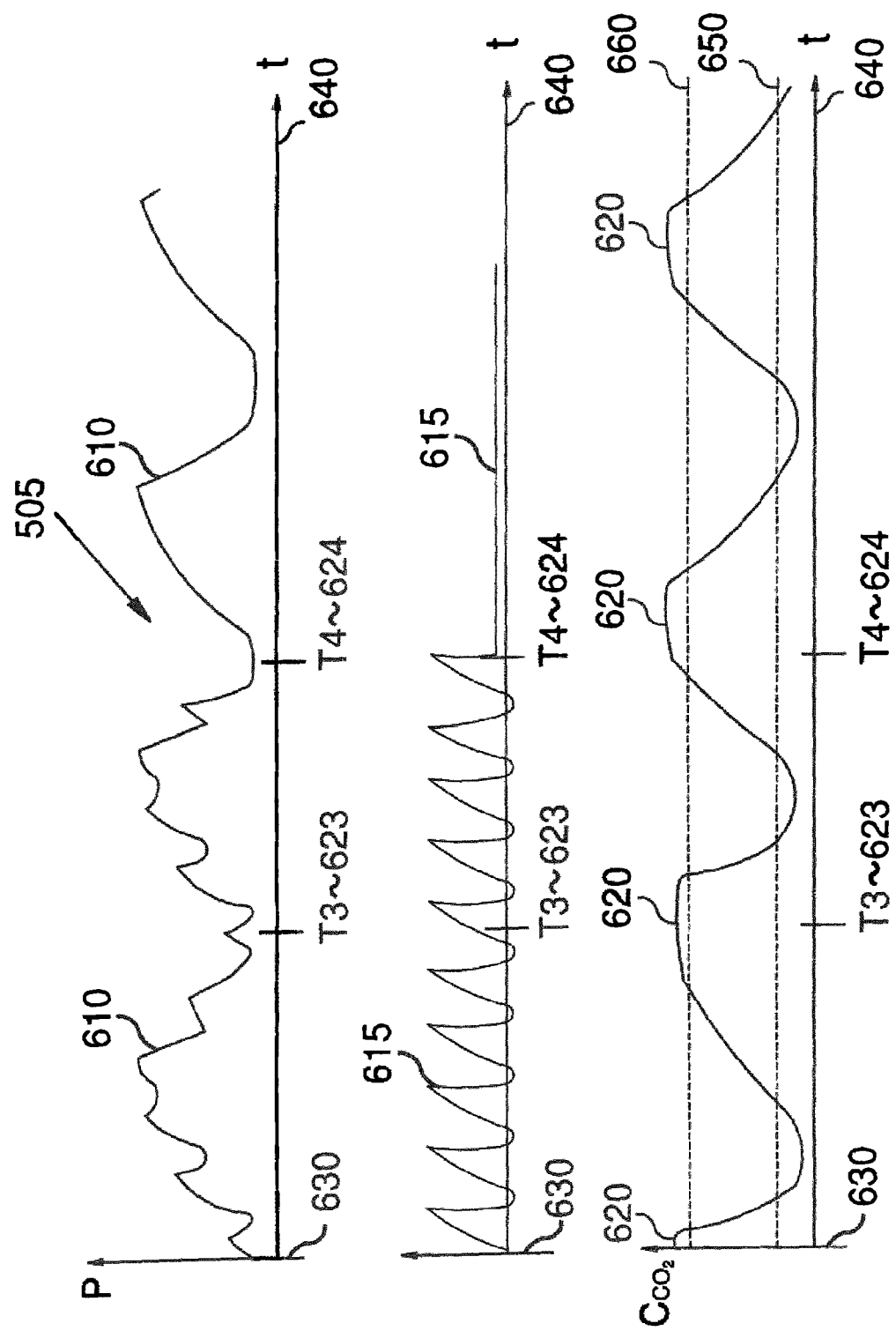
FIG. 5e is a diagram showing time curves of the ventilation pressure, cardiac massage (CM) and $CO_2$ measurement, chronologically following the time curve of FIG. 5d.

In these exemplary diagrams of the time curves 501, 502, 503, 504, 505 of the mechanical ventilation of a patient with simultaneously performed cardiac massage (CM), FIG. 5e showing the time curve 505 that follows chronologically the curve 504 of the mechanical ventilation of a patient with simultaneously performed cardiac massage (CM) according to FIG. 5d.

In the diagram 505 according to FIG. 5e, the time curve shows that the $CO_2$ concentration rises at a third time T3 623 to above the second predetermined threshold value 660 into the third concentration range of the $CO_2$ concentration 665, which indicates that the cardiovascular function can again be maintained in a stable form by the patient himself. The cardiac massage (CM) is ended in the further course at a fourth time T4 624, chronologically following the third time T3 623. The fact that the $CO_2$ concentration of the patient remains above the second predetermined threshold value 660 in the further course following the fourth time T4 624 can be considered to be a further indicator that the patient can now maintain his cardiovascular function again in a stable form on his own.

In the process 1000 (FIG. 4) of the ventilation with temporary application of cardiac massage (CM) according to FIGS. 5a through 5e, some alarm limits of the ventilator 1, 1' (FIGS. 1a, 1b) are adjusted or faded out by a corresponding adaptation device 46 (FIG. 2). This occurs during the operation of the ventilator with assisted cardiopulmonary resuscitation (CPR) in such a way or the acoustic alarm is preferably "muted," so that the user is not burdened in a disturbing manner during the ventilation, during the application of the cardiac massage (CM) and during the treatment of the patient.

Furthermore, the monitoring of the instances in which the first predetermined threshold value 650 is exceeded or not reached and the monitoring of the instances in which the second predetermined threshold value 660 is exceeded or not reached are preferably provided with a filtering, so that the changes into or out of the operation of the ventilator with assisted cardiopulmonary resuscitation (CPR) and the messages (FIG. 4) to the user cannot take place excessively frequently during the instances in which the threshold value is exceed or not reached. This filtering may be performed, for example, as amplitude filtering, mean value filtering or median filtering directly on the value of the $CO_2$ concentration or on values derived therefrom, and a time-based filtering with a monitoring time window is likewise possible. The monitoring time window may be, for example, such that changes in the $CO_2$ concentration values must last for a certain time before changeovers into or out of the operation of the ventilator with assisted cardiopulmonary resuscitation (CPR) are performed or messages (FIG. 4) are sent to the user. Besides the adaptation of the output of messages (FIG. 4) during the operation of the ventilator with assisted cardiopulmonary resuscitation (CPR), it is, furthermore, advantageous that the regulation does not respond to changes in the measured ventilation pressure (FIG. 2), which are caused by the cardiac massage (CM), during a pressure-controlled mode of ventilation, for example, CPAP, BiPAP, PC-PPS, PC-PS. The measured ventilation pressure is advantageously filtered and/or delayed for this during the operation of the ventilator 1, 1' (FIGS. 1, 1b) with assisted cardiopulmonary resuscitation (CPR) by means of suitable adaptation and delay elements 33, 32 (FIG. 2). This filtering may be performed, for example, as amplitude filtering, mean value filtering or median filtering directly on the measured value of the ventilation pressure (FIG. 2) or on values derived therefrom, as well as also in the further course of the signal processing, for example, before or on return into the control circuit. Time-based filtering is likewise possible with a monitoring time window. The monitoring time window may be, for example, such that changes in the values dP 35 (FIG. 2) of the ventilation pressure must last for a certain time before an adjustment (FIG. 2) of the ventilation pressure is performed by the control circuit. Oscillation buildup, transient oscillation or overshooting, or even a rise of the ventilation pressure as a response to the cardiac massage (CM) is prevented hereby.

Figure 6:
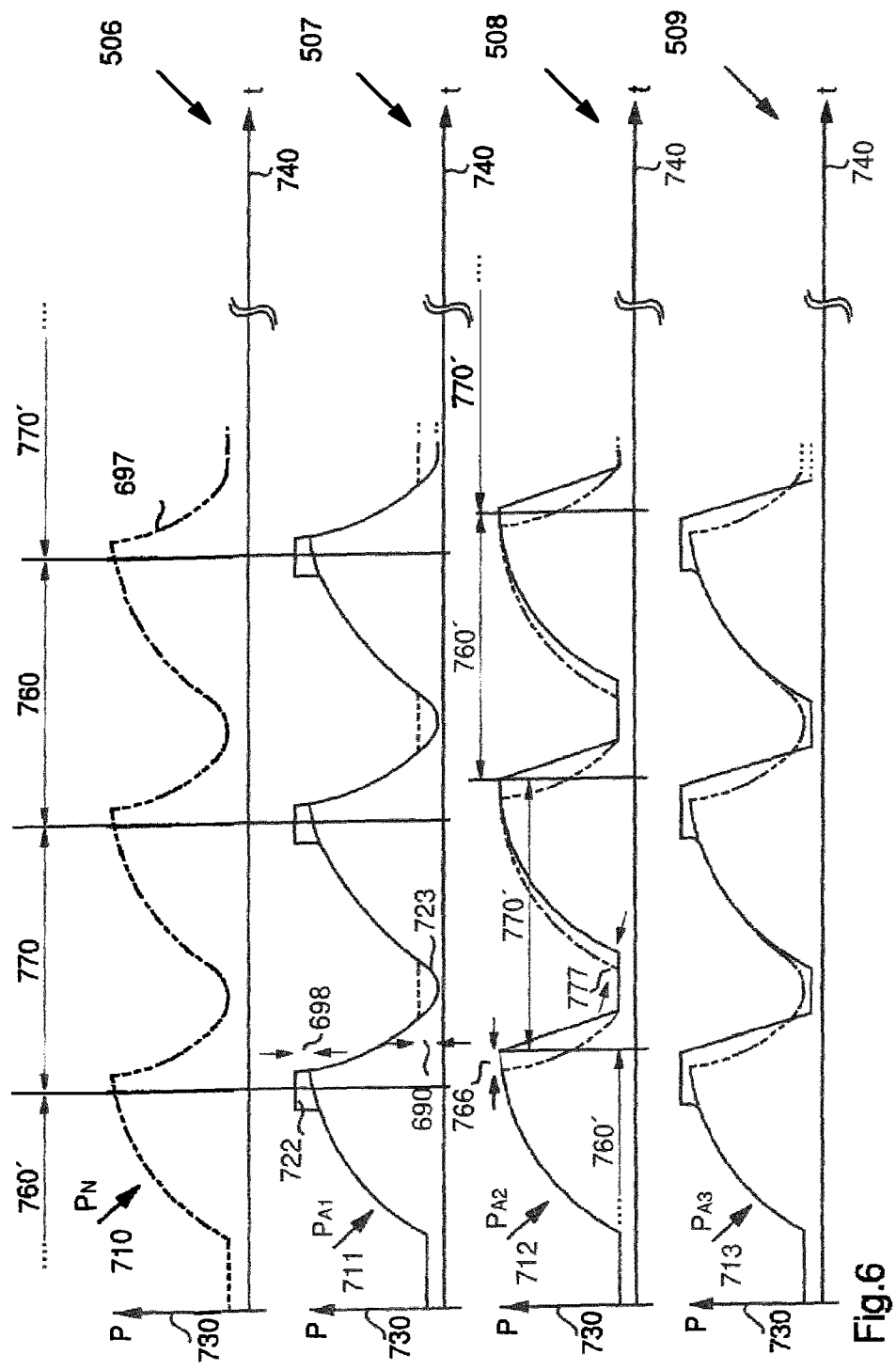
FIG. 6 is a diagram of the time course of ventilation during the operation of a ventilator with and without assisted cardiopulmonary resuscitation (CPR)

In a coordinate system with an abscissa 740 and an ordinate 730, FIG. 6 shows in the diagrams 506, 507, 508, 509 time curves of the ventilation of a patient during the operation of a ventilator with and without assisted cardiopulmonary resuscitation (CPR) (first and second modes of operation). The diagram shows a variation of the ventilation pressure during the operation of the ventilator with assisted cardiopulmonary resuscitation (CPR) (second mode of operation) compared to the operation of the ventilator without assisted cardiopulmonary resuscitation (CPR) (first mode of operation). In diagram 506, a curve drawn in broken line shows a normal time curve of the ventilation pressure PN 710 of a mechanically ventilated patient as the alternation of inspiration and expiration, as it is seen during the normal operation of a ventilator without assisted cardiopulmonary resuscitation (CPR). The ventilation pressure PN 710 is regulated by a control and regulation unit 7 (FIGS. 1*a*, 1*b*) during the normal operation of the ventilator 1, 1' (FIGS. 1*a*, 1*b*) without assisted cardiopulmonary resuscitation (CPR) (first mode of operation) by a current value 610 (4) of the ventilation pressure, which is detected by a pressure sensor 13 (FIGS. 1*a*, 1*b*), yielding a desired value for an actuation by a comparison with a first predetermined value 697, 16 (FIGS. 1*a*, 1*b*) and by the control and regulation unit 7 (FIGS. 1*a*, 1*b*) actuating an expiration valve 3 (FIGS. 1*a*, 1*b*) and an inspiration valve 2 (FIGS. 1*a*, 1*b*) on the basis of the comparison such that the current value 610 of the ventilation pressure corresponds essentially to the first predetermined value 697, 16 (FIGS. 1*a*, 1*b*). In the sense of the present invention, the first predetermined value is not only an individual value, to which the control and regulation unit 7 (FIGS. 1*a*, 1*b*) regulates, but a chronological sequence of predetermined desired values, e.g., in the form of a ventilation curve or of a course for controlling the ventilation. The pressure of the gas exhaled by the patient at the patient port is described by a first pressure time relationship (a first curve), and the flow control device is actuated during an inspiration phase such that the pressure of the gas supplied to the patient at the patient port is described by a second pressure time relationship (a second curve), wherein the expiration phase and the inspiration phase follow each other in a continuously alternating manner. Diagram 507 in FIG. 6 shows, by a curve drawn in solid line, a first alternative time curve 711 of the ventilation pressure $P_{A1}$ of a mechanically ventilated patient as the alternation of inspiration and expiration, as it is seen during the operation of a ventilator with assisted cardiopulmonary resuscitation (CPR). The control and regulation unit is configured such that in the second mode of operation the flow control device is actuated during the expiration phase such that the pressure of the gas exhaled by the patient at the patient port is described by a third pressure time relationship (a third curve), which pressure is increased compared to the first pressure time relationship, at least during a section of the expiration phase. In the second mode the flow control device is actuated during an inspiration phase such that the pressure of the gas supplied to the patient at the patient port is described at least during a section of the inspiration phase by a fourth pressure time relationship (a fourth curve), which pressure is reduced compared to the second pressure time relationship. The course of the normal ventilation pressure 710 according to the diagram 506 is also shown as a curve drawn in broken line in this diagram 507 to highlight the differences between the first alternative time curve 711 and the normal time curve 710.

Just as it was described before for the normal operation of the ventilator 1, 1' (FIG. 1*a*, 1*b*), the ventilation pressure $P_A$ 711 is adjusted by the control and regulation unit 7 (FIGS. 1*a*, 1*b*) to the first predetermined value 697, 16 (FIGS. 1*a*, 1*b*) during the operation of the ventilator 1, 1' (FIGS. 1*a*, 1*b*) with assisted cardiopulmonary resuscitation (CPR), with the peculiarity that the expiration valve 3 (FIGS. 1*a*, 1*b*) and the inspiration valve 2 (FIGS. 1*a*, 1*b*) are actuated by the control and regulation unit 7 (FIGS. 1*a*, 1*b*) in a special manner such that a pressure $P_H$ 722 increased by a second predetermined value 698 is obtained at the start of the expiration phase of the first cycle 760 of the ventilation, and that a pressure $P_L$ 723 reduced by a third predetermined value 690 is obtained at the start of the inspiration phase of the second cycle 770 of the ventilation. In addition, a diagram 508 in FIG. 6 shows a curve drawn in solid line, which represents a second alternative time curve 712 of the ventilation pressure $P_{A2}$ of a mechanically ventilated patient as the alternation of inspiration and expiration, as it is seen during the operation of a ventilator with assisted cardiopulmonary resuscitation (CPR) (second mode of operation). The curve describing the normal ventilation pressure 710 according to diagram 506 is also shown as a curve drawn in broken line in this diagram 508 to highlight the differences between the second alternative time curve 712 and the normal time curve 710. Just as it was described before for the normal operation of the ventilator 1, 1' (FIGS. 1*a*, 1*b*), the ventilation pressure $P_A$ 712 is adjusted by the control and regulation unit 7 (FIGS. 1*a*, 1*b*) during the operation of the ventilator 1, 1' (FIGS. 1*a*, 1*b*) with assisted cardiopulmonary resuscitation (CPR) (second mode of operation) to the first predetermined value 697, 16 (FIGS. 1*a*, 1*b*), with the peculiarity that the expiration valve 3 (FIGS. 1*a*, 1*b*) and the inspiration valve 2 (FIGS. 1*a*, 1*b*) are actuated by the control and regulation unit 7 (FIGS. 1*a*, 1*b*) such that the first cycle 760' prolonged in time by a second predetermined time value 766 is obtained at the start of the expiration phase of the first cycle 760 of the ventilation, and that the second cycle 770' shifted in time by a third predetermined time value 777 is obtained at the start of the inspiration phase of the second phase 770 of the ventilation. Furthermore, a diagram 509 in the form of a curve drawn in broken line in FIG. 6 represents a third alternative time curve 713 of the ventilation pressure $P_{A3}$ of a mechanically ventilated patient, as it is obtained from a combination of the first alternative curve 711 from diagram 507 and the second alternative curve 712 from diagram 508 during the operation of a ventilator with assisted cardiopulmonary resuscitation (CPR). The curve describing the normal ventilation pressure 710 according to diagram 506 is also shown as a curve drawn in broken line in this diagram 509 to highlight the differences between the third alternative time curve 713 and the normal time curve 710.

Figure 7A:
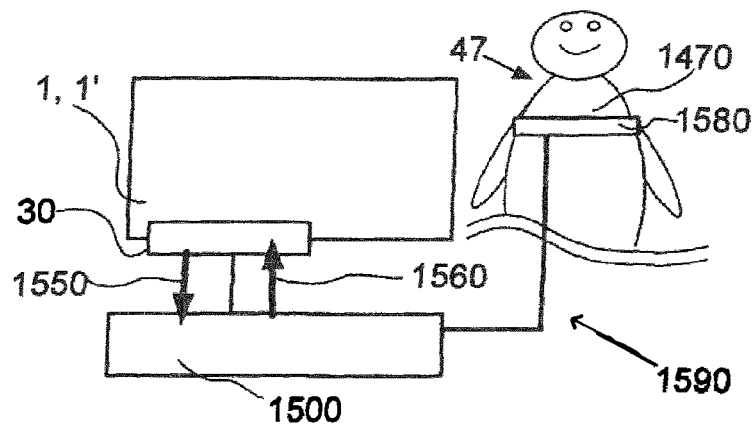
FIG. 7a is a schematic overview of a medical system with a ventilator according to FIG. 1a or FIG. 1b and with an assist device for the automatic performance of cardiac massage (CM)

FIG. 7*a* shows in a schematic overview a medical system 1590 with a ventilator 1, 1' according to FIG. 1*a* or FIG. 1*b* and with an assist device 1500 for automatically performing a cardiac massage (CM). The assist device 1500 is connected to the chest 1470 of a patient 47 by means of a compression element 1550. The assist device 1500 is connected to the ventilator 1, 1' via a sensor and data interface 30. The assist device 1500 sends a control signal 1560 to the ventilator 1, 1' via the sensor and data interface 30 in order to bring the ventilator 1, 1' into a state of pause or to start or end an operation of the ventilator 1, 1' with assisted cardiopulmonary resuscitation (CPR) or to bring about a change in an alarm generation on the ventilator 1, 1'. The ventilator 1, 1' is able to bring the assist device 1500 into a state of pause by means of an additional control signal 1550.

Figure 7B:
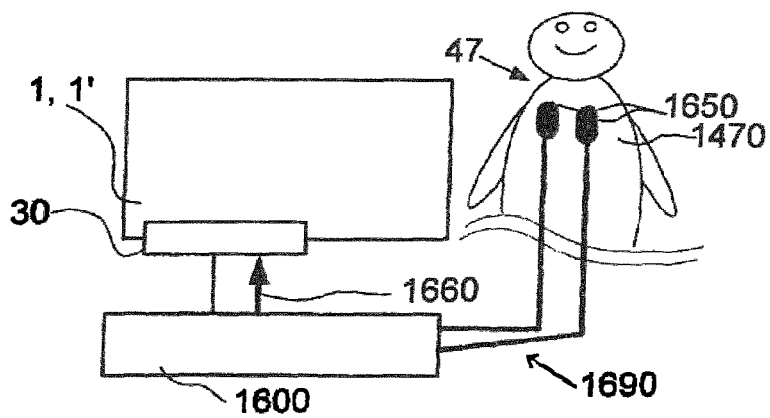
FIG. 7b is a schematic overview of a medical system with a ventilator according to FIG. 1a or FIG. 1b and with a voltage generator suitable for resuscitation.

FIG. 7*b* schematically shows a medical system 1690 with a ventilator 1, 1' according to FIG. 1*a* or FIG. 1*b* and with a voltage generator/defibrillator 1600 suitable for resuscitation. The voltage generator 1600 is connected to the chest 1470 of a patient 47 by means of electrodes 1650. The voltage generator 1600 is connected to the ventilator 1, 1' via a sensor and data interface 30. The voltage generator 1600 sends a control signal 1660 to the ventilator 1, 1' via the sensor and data interface 30 in order to bring the ventilator 1, 1' into a state of pause or to bring about a change in an alarm generation on the ventilator 1, 1'.

While specific embodiments of the invention have been shown and described in detail to illustrate the application of the principles of the invention, it will be understood that the invention may be embodied otherwise without departing from such principles.

The invention claimed is:

1. A ventilation system comprising:
a gas supply device;
a tube arrangement, wherein the tube arrangement has a patient port for connection to a patient in order to send gas from the gas supply device to the patient and in order to remove gas exhaled by the patient;
a flow control device for controlling the gas flow from the gas supply device to the patient port and for controlling the gas flow away from the patient port;
a sensor unit, which is arranged in the tube arrangement and is set up to detect parameters of the gas supplied to the patient and exhaled by the patient;
a control and regulation unit for controlling the gas supply device and the flow control device, which control and regulation unit is connected to the gas supply device, to the flow control device, and to the sensor unit, wherein:
the control and regulation unit is configured to ensure that in a first mode of operation, the flow control device is actuated during an expiration phase such that the pressure of the gas exhaled by the patient at the patient port is described by a first pressure time relationship, and the flow control device is actuated during an inspiration phase such that the pressure of the gas supplied to the patient at the patient port is described by a second pressure time relationship, wherein the expiration phase and the inspiration phase follow each other in a continuously alternating manner;
the control and regulation unit is configured to have a second mode of operation;
the control and regulation unit is configured such that in the second mode of operation the flow control device is actuated during the expiration phase such that the pressure of the gas exhaled by the patient at the patient port is described by a third pressure time relationship, which is increased compared to the first pressure time relationship, at least during a section of the expiration phase; and
the flow control device is actuated during an inspiration phase such that the pressure of the gas supplied to the patient at the patient port is described at least during a section of the inspiration phase by a fourth pressure time relationship, which is reduced compared to the second pressure time relationship; and
a switchover device for switching over the control and regulation unit between the first and second modes of operation, wherein:
the sensor unit has a sensor, which is configured to determine the $CO_2$ content in the air exhaled by the patient during the expiration phase;
the control and regulation unit is configured to determine, from the $CO_2$ content in the air exhaled by the patient, whether a cardiopulmonary resuscitation is being performed on the patient; and
the control and regulation unit is configured to select the second mode of ventilation operation when it is determined, from the $CO_2$ content in the air exhaled by the patient, that a cardiopulmonary resuscitation is being performed.

2. A ventilation system in accordance with claim 1, wherein:
the control and regulation unit is configured to actuate the flow control device such that the expiration phase and the inspiration phase each have two consecutive partial phases, a first partial phase and a second partial phase, in the second mode of ventilation operation;
the pressure of the gas exhaled by the patient at the patient port is described by the third pressure time relationship during the first partial phase of the expiration phase;
the pressure of the gas exhaled by the patient at the patient port is described by a pressure time relationship corresponding to the first pressure time relationship during the second partial phase of the expiration phase;
the pressure of the gas supplied to the patient at the patient port is described by the fourth pressure time relationship during the first partial phase of the inspiration phase; and
the pressure of the gas supplied to the patient at the patient port is described by a pressure time relationship corresponding to the second pressure time relationship during the second partial phase of the inspiration phase.

3. A ventilation system in accordance with claim 1, wherein the control and regulation unit is configured to actuate the flow control device during the expiration phase such that the third pressure time relationship of the pressure is obtained by increasing a desired pressure value.

4. A ventilation system in accordance with claim 1, wherein the control and regulation unit is configured to actuate the flow control device during the inspiration phase such that the fourth pressure time relationship of the pressure is obtained by reducing a desired pressure value.

5. A ventilation system in accordance with claim 1, wherein:
the tube arrangement has a breathing gas outlet line, which leads away from the patient port and can be opened and closed in relation to the patient port by an expiration valve of the flow control device;
the expiration valve is connected to the control and regulation unit; and
the control and regulation unit is configured to actuate the expiration valve during the expiration phase such that it is opened with a time delay relative to the start of the expiration phase.

6. A ventilation system in accordance with claim 1, wherein:
the tube arrangement has a breathing gas supply line, which leads from the gas supply unit to the patient port and can be opened and closed in relation to the patient port by an inspiration valve of the flow control device;
the inspiration valve is connected to the control and regulation unit; and
the control and regulation unit is configured to actuate the inspiration valve during the inspiration such that it is opened with a time delay relative to the start of the inspiration phase.

7. A ventilation system in accordance with claim 1, wherein the switchover device is provided comprising a user input, with which a user can switch over the control and regulation unit between the first mode of ventilation operation and the second mode of ventilation operation.

8. A ventilation system in accordance with claim 1, further comprising:
a display unit, which is connected to the control and regulation unit, wherein:
the control and regulation unit is configured such that a first alarm message is sent to the display device in the first mode of ventilation operation when a parameter detected by the sensor unit exceeds or falls below a threshold value; and the control and regulation unit is configured not to send an alarm message or to send a second alarm message different from the first alarm message in the second mode of ventilation operation when the parameter detected by the sensor unit exceeds or falls below the threshold value.

9. A ventilation system in accordance with claim 8, wherein:
the display unit has an acoustic signal device for generating an acoustic alarm;
the first alarm message comprises a first acoustic alarm; and
the second alarm message does not comprise an acoustic alarm or comprises a second acoustic alarm, which is different from the first acoustic alarm and the second acoustic alarm has a volume that is reduced compared to that of the first acoustic alarm.

10. A ventilation system in accordance with claim 1, further comprising:
a display unit, wherein:
the control and regulation unit is configured to monitor a parameter detected by the sensor unit in the second mode of ventilation operation, and to trigger a first message by the display unit when the parameter falls below a first threshold value, to trigger a second message by the display unit when the parameter exceeds the first threshold value and falls below a second threshold value that is higher than the first threshold value, and to trigger a third message by the display unit when the parameter exceeds the second threshold value; and
the first, second and third messages are different from one another.

11. A ventilation system in accordance with claim 1, further comprising a device for automatically performing a cardiopulmonary resuscitation.

12. A ventilation system in accordance with claim 1, further comprising a voltage generator for generating voltage pulses, which voltage generator is connected to the control and regulation unit, wherein the voltage generator is provided with electrodes for connection to a patient.

13. A ventilation system comprising:
a gas supply device;
a tube arrangement, wherein the tube arrangement has a patient port for connection to a patient in order to send gas from the gas supply device to the patient and in order to remove gas exhaled by the patient;
a flow control device for controlling the gas flow from the gas supply device to the patient port and for controlling the gas flow away from the patient port;
a sensor unit, which is arranged in the tube arrangement and is set up to detect parameters of the gas supplied to the patient and exhaled by the patient;
a control and regulation unit for controlling the gas supply device and the flow control device, which control and regulation unit is connected to the gas supply device, to the flow control device, and to the sensor unit, wherein:
the control and regulation unit is configured to ensure that in a first mode of operation, the flow control device is actuated during an expiration phase such that the pressure of the gas exhaled by the patient at the patient port is described by a first pressure time relationship, and the flow control device is actuated during an inspiration phase such that the pressure of the gas supplied to the patient at the patient port is described by a second pressure time relationship, wherein the expiration phase and the inspiration phase follow each other in a continuously alternating manner;
the control and regulation unit is configured to have a second mode of operation;
the control and regulation unit is configured such that in the second mode of operation the flow control device is actuated during the expiration phase such that the pressure of the gas exhaled by the patient at the patient port is described by a third pressure time relationship, which is increased compared to the first pressure time relationship, at least during a section of the expiration phase; and
the flow control device is actuated during an inspiration phase such that the pressure of the gas supplied to the patient at the patient port is described at least during a section of the inspiration phase by a fourth pressure time relationship, which is reduced compared to the second pressure time relationship;
a switchover device for switching over the control and regulation unit between the first and second modes of operation, wherein:
sensor unit has a sensor for measuring the oxygen saturation in the blood ($SPO_2$), which sensor can be connected to a patient;
the control and regulation unit is configured to determine from the value of the oxygen saturation in the blood whether a cardiopulmonary resuscitation is being performed on the patient; and
the control and regulation unit is configured to select the second mode of ventilation operation when it is determined, from oxygen saturation in the blood, that a cardiopulmonary resuscitation is being performed.

14. A ventilation system comprising:
a gas supply device;
a tube arrangement, wherein the tube arrangement has a patient port for connection to a patient in order to send gas from the gas supply device to the patient and in order to remove gas exhaled by the patient;
a flow control device for controlling the gas flow from the gas supply device to the patient port and for controlling the gas flow away from the patient port;
a sensor unit, which is arranged in the tube arrangement and is set up to detect parameters of the gas supplied to the patient and exhaled by the patient;
a control and regulation unit for controlling the gas supply device and the flow control device, which control and regulation unit is connected to the gas supply device, to the flow control device, and to the sensor unit, wherein:
the control and regulation unit is configured to ensure that in a first mode of operation, the flow control device is actuated during an expiration phase such that the pressure of the gas exhaled by the patient at the patient port is described by a first pressure time relationship, and the flow control device is actuated during an inspiration phase such that the pressure of the gas supplied to the patient at the patient port is described by a second pressure time relationship, wherein the expiration phase and the inspiration phase follow each other in a continuously alternating manner;
the control and regulation unit is configured to have a second mode of operation;
the control and regulation unit is configured such that in the second mode of operation the flow control device is actuated during the expiration phase such that the pressure of the gas exhaled by the patient at the patient port is described by a third pressure time relationship, which is increased compared to the first pressure time relationship, at least during a section of the expiration phase; and the flow control device is actuated during an inspiration phase such that the pressure of the gas supplied to the patient at the patient port is described at least during a section of the inspiration phase by a fourth pressure time relationship, which is reduced compared to the second pressure time relationship; and a switchover device for switching over the control and regulation unit between the first and second modes of operation, wherein:

the sensor unit has a sensor, which is configured to determine the oxygen content in the air exhaled by the patient during the expiration phase;

the control and regulation unit is configured to determine from the oxygen content in the air exhaled by the patient whether a cardiopulmonary resuscitation is being performed on the patient; and the control and regulation unit is configured to select the second mode of ventilation operation when it is determined, from the oxygen content in the air exhaled by the patient, that a cardiopulmonary resuscitation is being performed.

\* \* \* \* \*